(12) United States Patent
Suen et al.

(10) Patent No.: US 9,752,093 B2
(45) Date of Patent: Sep. 5, 2017

(54) BORATED POLYOL ESTER OF HINDERED PHENOL ANTIOXIDANT/FRICTION MODIFIER WITH ENHANCED PERFORMANCE

(71) Applicants: Yat Fan Suen, Albany, CA (US); Julian H. McLain, Seattle, WA (US); John Robert Miller, San Rafael, CA (US); Jennifer Elizabeth Newell, San Francisco, CA (US); Shengua Li, Fremont, CA (US); Vivek Palekar, Pleasanton, CA (US)

(72) Inventors: Yat Fan Suen, Albany, CA (US); Julian H. McLain, Seattle, WA (US); John Robert Miller, San Rafael, CA (US); Jennifer Elizabeth Newell, San Francisco, CA (US); Shengua Li, Fremont, CA (US); Vivek Palekar, Pleasanton, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 1 day.

(21) Appl. No.: 14/730,587

(22) Filed: Jun. 4, 2015

(65) Prior Publication Data
US 2016/0355746 A1 Dec. 8, 2016

(51) Int. Cl.
*C10M 139/00* (2006.01)
*C10M 159/12* (2006.01)
*C07F 5/02* (2006.01)

(52) U.S. Cl.
CPC ........... *C10M 139/00* (2013.01); *C07F 5/025* (2013.01); *C10M 159/12* (2013.01); *C10M 2207/023* (2013.01); *C10M 2207/026* (2013.01); *C10M 2207/281* (2013.01); *C10M 2207/283* (2013.01); *C10M 2207/289* (2013.01); *C10M 2227/061* (2013.01); *C10M 2227/062* (2013.01); *C10N 2230/06* (2013.01); *C10N 2230/10* (2013.01); *C10N 2230/12* (2013.01); *C10N 2230/52* (2013.01); *C10N 2230/54* (2013.01); *C10N 2240/04* (2013.01); *C10N 2240/08* (2013.01); *C10N 2240/10* (2013.01); *C10N 2240/102* (2013.01); *C10N 2270/02* (2013.01)

(58) Field of Classification Search
CPC ............ C10N 2230/06; C10N 2230/10; C10N 2230/12; C10N 2230/52; C10N 2230/54; C10N 2240/04; C10N 2240/08; C10N 2240/10; C10N 2240/102; C10N 2270/02; C10M 2207/023; C10M 2207/026; C10M 2207/281; C10M 2207/283; C10M 2207/289; C10M 2227/061; C10M 2227/062; C10M 139/00; C10M 159/12; C07F 5/025
See application file for complete search history.

(56) References Cited

U.S. PATENT DOCUMENTS 5,698,499 A * 12/1997 Baranski ................... C07F 5/04
508/198

OTHER PUBLICATIONS

Chamberland, "Synthesis of Potential Early-Stage Intermediates in the Biosynthesis of FR900482 and Mitomycin C," Organic Letters, 2009, vol. 11, No. 4, 791-S47.*
Appendino et al., "Structure-Activity Relationships of the Estrogenic Sesquiterpene Ester Ferutinin. Modification of the Terpenoid Core." J. Nat. Prod. 2004, 67, 1557-1564.*

* cited by examiner

*Primary Examiner* — Paul A Zucker
*Assistant Examiner* — Mark Luderer
(74) *Attorney, Agent, or Firm* — Carlton Virassammy

(57) ABSTRACT

The present invention is directed to compounds comprising the reaction products of a phenolic ester polyol, a boron containing compound, and optionally, an alcohol. Also disclosed are compounds comprising the reaction products of a polyol, a boron containing compound, and a phenolic acid or ester.
Lubricating oil compositions and additive concentrates comprising above compounds, and methods for operating an internal combustion engine using said lubricating oil compositions are also disclosed.

15 Claims, No Drawings

BORATED POLYOL ESTER OF HINDERED PHENOL ANTIOXIDANT/FRICTION MODIFIER WITH ENHANCED PERFORMANCE

FIELD OF THE INVENTION

The present invention generally relates to a borated polyol hindered phenol antioxidant/friction modifier and compositions containing same.

BACKGROUND OF THE INVENTION

The demand on engine lubricants has become more severe to cope with modern engine design with ever stronger anti-oxidation requirements. Thus, this forces additive companies to develop robust engine oils with stronger antioxidant and anti-nitration additives. Further to this is the firmly established issue of fuel economy which has become a very import issue for automotive manufacturers, lubricant additive companies, and automobile owners. Thus reducing friction between moving parts in the engine is paramount.

Primary antioxidants have long been part of lubricant additive formulations. They have been widely used to improve the thermal-oxidative stability and/or light induced oxidative degradation in numerous products used in engineering. For example, primary antioxidants can improve the performance properties in lubricants, hydraulic fluids, metal working fluids, fuels or polymers, just to name a few. Hindered phenolic anti-oxidants, a class of primary antioxidants, are capable of donating a hydrogen atom that reacts with alkyl radicals or peroxy radicals, thus interrupting the radical chain mechanism of the auto-oxidation process which results in the hindered phenol becoming a stable radical.

Furthermore, engine oil acts as a lubricant between moving engine parts at various conditions of load, speed and temperature. Hence, the various engine components experience different combinations of boundary layer, mixed, and (elasto) hydrodynamic regimes of lubrication. The largest frictional losses occur at piston liner/piston ring interfaces and a smaller part by the bearings and valve train. To reduce the energy losses due to friction of the various engine parts and to prevent engine wear, additives such as friction modifiers, anti-wear agents, and antioxidants are incorporated into the engine oil. Antioxidants tend to lengthen the effect of the afore-mentioned additives. Further, to reduce the hydrodynamic friction in the piston/cylinder, the viscosity of engine oils has been lowered. This has resulted in an increased the dependence on friction modifiers to offset the new boundary layer regime. Hence, a vast amount of effort has focused on the interaction of oil viscosity with various friction modifiers to improve fuel economy.

Although compounds combining boron with anti-oxidants are known in the art, as evidenced by EP 0089844, U.S. Pat. No. 3,347,793, U.S. Pat. No. 3,356,707, U.S. Pat. No. 3,359,298, U.S. Pat. No. 3,509,054, U.S. Pat. No. 4,474,670, U.S. Pat. No. 5,252,237, U.S. Pat. No. 5,698,499, U.S. Pat. No. 6,605,572, and U.S. Pat. No. 6,777,378; compounds with the outstanding oxidation and friction performance of those of the invention have not been described.

Thus, herein we report borated polyol hindered phenol antioxidant/friction modifier compounds and compositions containing same. These compounds and compositions enhanced performance in engine oils when compared with industry standard hindered phenolic antioxidants.

SUMMARY OF THE INVENTION

In accordance with one embodiment of the present invention, there is provided a compound comprising the reaction product of:
  a. a phenolic ester polyol,
  b. a boron containing compound, and
  c. optionally, an alcohol.

In another embodiment of the present invention, there is provided a compound comprising the reaction product of:
  a. a polyol,
  b. a boron containing compound, and
  c. a phenolic acid or ester.

Also provided are lubricating oil compositions and additive concentrates comprising above compounds, and methods for operating an internal combustion engine using said lubricating oil compositions.

Definitions

The following terms will be used throughout the specification and will have the following meanings unless otherwise indicated.

The term "a major amount" of a base oil refers to where the amount of the base oil is at least 40 wt. % of the lubricating oil composition. In some embodiments, "a major amount" of a base oil refers to an amount of the base oil more than 50 wt. %, more than 60 wt. %, more than 70 wt. %, more than 80 wt. %, or more than 90 wt. % of the lubricating oil composition.

In the following description, all numbers disclosed herein are approximate values, regardless whether the word "about" or "approximate" is used in connection therewith. They may vary by 1 percent, 2 percent, 5 percent, or, sometimes, 10 to 20 percent.

DETAILED DESCRIPTION OF THE INVENTION

In an aspect the present invention provides a borated compound that demonstrates both antioxidant and anti-friction properties.

In one embodiment, the present invention provides a compound comprising the reaction product of a boron containing compound, a phenolic ester polyol, and an alcohol.

In one embodiment, the present invention provides a compound comprising the reaction product of a boron containing compound and a phenolic ester polyol.

In one embodiment, the present invention provides a compound comprising the reaction product of a boron containing compound, a polyol, and a phenolic acid or ester.

In general, the phenolic ester polyol of the present invention is formed through the transesterification of 3, 5-dialkyl-4-hydroxy phenyl alkanoate with a polyol. In one embodiment, the phenolic ester polyol is a compound having the following formula (I):

Formula (I)

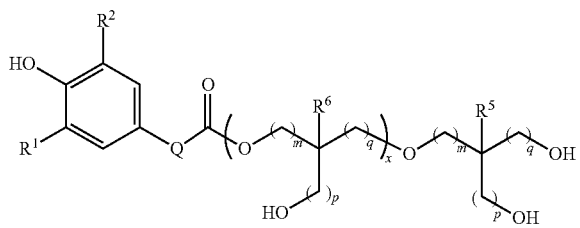

wherein Q is an alkylene group of 2 to 6 carbon atoms; each m is independently 1, 2, or 3; each p is independently 0, 1, 2, or 3; each q is independently 0, 1, 2, or 3; x is 0, 1, or 2; $R^1$ and $R^2$ are each independently a $C_1$-$C_{12}$ alkyl group; $R^5$ is H, a $C_1$-$C_{12}$ alkyl group, or a $C_1$-$C_3$ alkanol; and $R^6$ is H, a $C_1$-$C_{12}$ alkyl group, or a $C_1$-$C_3$ alkanol.

The alkylene group may be straight or branched chain, exemplarily including ethylene group, propylene group (1-methylethylene group, 2-methylethylene group), trimethylene group, butylene group (1-ethylethylene group, 2-ethylethylene group), 1,2-dimethylethylene group, 2,2-dimethylethylene group, 1-methyltrimethylene group, 2-methyltrimethylene group, 3-methyltrimethylene group, tetramethylene group, pentylene group, 1-ethyl-1-methylethylene group, 1-ethyl-2-methylethylene group, 1,1,2-trimethylethylene group, 1,2,2-trimethylethylene group, 1-ethyltrimethylene group, 2-ethyltrimethylene group, 3-ethyltrimethylene group, 1,1-dimethyltrimethylene group, 1,2-dimethyltrimethylene group, 1,3-dimethyltrimethylene group, 2,3-dimethyltrimethylene group, 3,3-dimethyltrimethylene group, 1-methyltetramethylene group, 2-methyltetramethylene group, 3-methyltetramethylene group, 4-methyltetramethylene group, pentamethylene group, hexylene group (1-butylethylene group, 2-butylethylene group), 1-methyl-1-propylethylene group, 1-methyl-2-propylethylene group, 2-methyl-2-propylethylene group, 1,1-diethylethylene group, 1,2-diethylethylene group, 2,2-diethylethylene group, 1-ethyl-1,2-dimethylethylene group, 1-ethyl-2,2-dimethylethylene group, 2-ethyl-1,1-dimethylethylene group, 2-ethyl-1,2-dimethylethylene group, 1,1,2,2-tetramethylethylene group, 1-propyltrimethylene group, 2-propyltrimethylene group, 3-propyltrimethylene group, 1-ethyl-1-methyltrimethylene group, 1-ethyl-2-methyltrimethylene group, 1-ethyl-3-methyltrimethylene group, 2-ethyl-1-methyltrimethylene group, 2-ethyl-2-methyltrimethylene group, 2-ethyl-3-methyltrimethylene group, 3-ethyl-1-methyltrimethylene group, 3-ethyl-2-methyltrimethylene group, 3-ethyl-3-methyltrimethylene group, 1,1,2-trimethyltrimethylene group, 1,1,3-trimethyltrimethylene group, 1,2,2-trimethyltrimethylene group, 1,2,3-trimethyltrimethylene group, 1,3,3-trimethyltrimethylene group, 2,2,3-trimethyltrimethylene group, 2,3,3-trimethyltrimethylene group, 1-ethyltetramethylene group, 2-ethyltetramethylene group, 3-ethyltetramethylene group, 4-ethyltetramethylene group, 1,1-dimethyltetramethylene group, 1,2-dimethyltetramethylene group, 1,3-dimethyltetramethylene group, 1,4-dimethyltetramethylene group, 2,2-dimethyltetramethylene group, 2,3-dimethyltetramethylene group, 2,4-dimethyltetramethylene group, 3,3-dimethyltetramethylene group, 3,4-dimethyltetramethylene group, 4,4-dimethyltetramethylene group, 1-methylpentamethylene group, 2-methylpentamethylene group, 3-methylpentamethylene group, 4-methylpentamethylene group, 5-methylpentamethylene group and hexamethylene group. Most preferred Q is 2-4 alkylene carbon atoms more preferably ethylene and methyl ethylene groups that may be made available with a minimum of reaction process steps and/or commercially available.

Several examples of the phenolic ester polyol include, but are not limited to, glycerol ester of a propionate phenol, diglycerol ester of a propionate phenol, pentaerythritol ester of a propionate phenol, and a trimethylolethane ester of a propionate phenol.

The boron compound may be any boron containing compound capable of boronating the oil soluble/dispersible phenolic ester polyol represented by Formula I. Suitable boron compounds include boron trioxide or any of the various forms of boric acid including metaboric acid ($HBO_2$), orthoboric acid ($H_3BO_3$) and tetraboric acid ($H_2B_4O_2$). Alkyl borates such as the mono-, di- and tri-$C_{1-6}$ alkyl borates may employ. Thus suitable alkyl borates are the mono-, di- and tri-methylborates; the mono-, di- and tri-ethylborates; the mono-, di- and tri-propylborates, and the mono-, di- and tri-butylborates and mixtures thereof. The particularly preferred boron compound is boric acid and especially orthoboric acid.

The alcohol employed can be a linear or branched aliphatic alcohol (monool) or polyol (i.e., diol, triol, tetraol). In an embodiment, the linear or branched aliphatic alcohol or polyol can have from 1 to 12 carbon atoms. Examples of alcohols of the present invention are, but not limited to methanol, ethanol, propanol, butanol, pentanol, hexanol, heptanol, octanol, nonanol, decanol, undecanol, dodecanol, ethylene glycol, trimethylene glycol, propylene glycol, glycerol, diglycerol, and pentaerythritol. In one embodiment, the alcohol is selected from the group consisting of 2-ethylhexanol, 1-octanol, and glycerol.

In general, the phenolic acid or ester of the present invention is a compound having the following formula (II):

(Formula II)

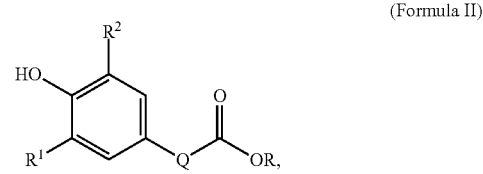

wherein Q is an alkylene group of 2 to 6 carbon atoms; R is H or a moiety suitable to undergo transesterification; $R^1$ and $R^2$ are each independently a $C_1$-$C_{12}$ alkyl group. In one embodiment, the moiety suitable to undergo transesterification is a methyl or ethyl group.

In general, the polyol of the present invention is a compound having the following formula (Formula III)

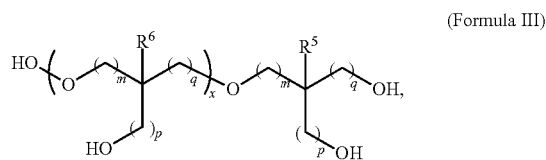

wherein each m is independently 1, 2, or 3; each p is independently 0, 1, 2, or 3; each q is independently 0, 1, 2, or 3; x is 0, 1, or 2; $R^5$ is H, a $C_1$-$C_{12}$ alkyl group, or a $C_1$-$C_3$ alkanol; and $R^6$ is H, a $C_1$-$C_{12}$ alkyl group, or a $C_1$-$C_3$ alkanol.

In an aspect, the present invention provides a compound having the following formula (IV):

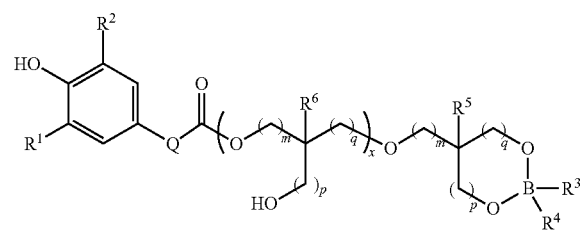

Formula (IV)

wherein Q is an alkylene group of 2 to 6 carbon atoms; each m is independently 1, 2, or 3; each p is independently 0, 1, 2, or 3; each q is independently 0, 1, 2, or 3; x is 0, 1, or 2; $R^1$ and $R^2$ are each independently a $C_1$-$C_{12}$ alkyl group; $R^3$ is absent or a $C_1$-$C_{12}$ alkoxy group; $R^4$ is absent or a $C_1$-$C_{12}$ alkoxy group; $R^5$ is H, a $C_1$-$C_{12}$ alkyl group, a $C_1$-$C_3$ alkanol; and $R^6$ is H, a $C_1$-$C_{12}$ alkyl group, or a $C_1$-$C_3$ alkanol. In one embodiment, $R^1$ and $R^2$ are both t-butyl groups. In another embodiment, $R^3$ and $R^4$ and the boron atom to which they are attached form a five to eight membered ring.

In an aspect, the present invention provides a compound having the following formula (V):

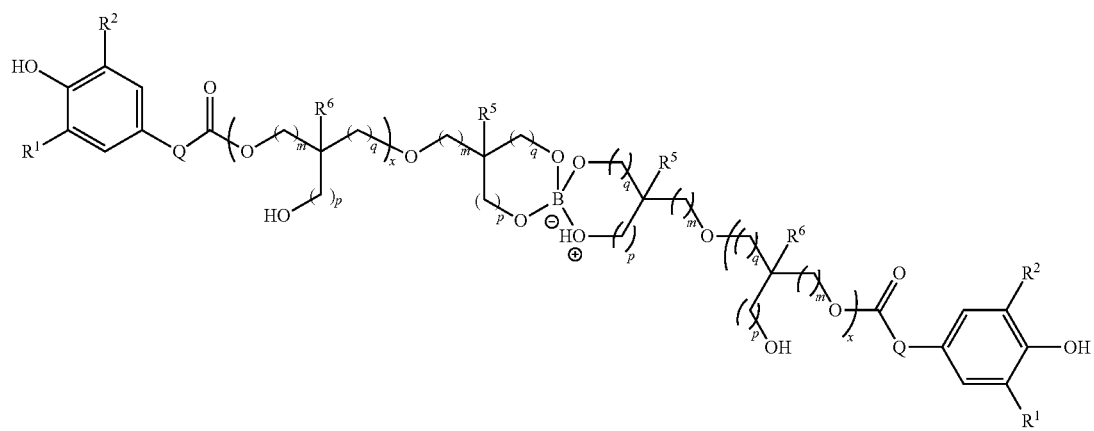

Formula (V)

wherein Q is an alkylene group of 2 to 6 carbon atoms; each m is independently 1, 2, or 3; each p is independently 0, 1, 2, or 3; each q is independently 0, 1, 2, or 3; x is 0, 1, or 2; $R^1$ and $R^2$ are each independently a $C_1$-$C_{12}$ alkyl group; $R^5$ is H, a $C_1$-$C_{12}$ alkyl group, or a $C_1$-$C_3$ alkanol; and $R^6$ is H, a $C_1$-$C_{12}$ alkyl group, or a $C_1$-$C_3$ alkanol. In one embodiment, $R^1$ and $R^2$ are both t-butyl groups.

In one embodiment, the present invention provides a compound having the following formula (VI):

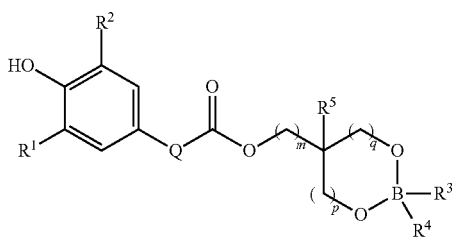

Formula (VI)

wherein Q is an alkylene group of 2 to 6 carbon atoms; each m is independently 1, 2, or 3; each p is independently 0, 1, 2, or 3; each q is independently 0, 1, 2, or 3; x is 0, 1, or 2; $R^1$ and $R^2$ are each independently a $C_1$-$C_{12}$ alkyl group; $R^3$ is absent or a $C_1$-$C_{12}$ alkoxy group; $R^4$ is absent or a $C_1$-$C_{12}$ alkoxy group; and $R^5$ is H, a $C_1$-$C_{12}$ alkyl group, or a $C_1$-$C_3$ alkanol. In one embodiment, $R^1$ and $R^2$ are both t-butyl groups.

In one embodiment, the present invention provides a compound having the following formula (VII):

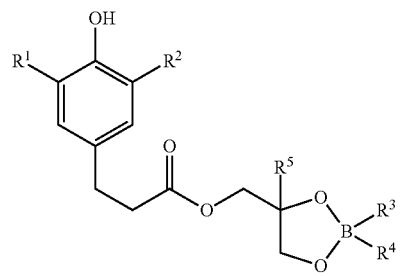

Formula (VII)

wherein $R^1$ and $R^2$ are each independently a $C_1$-$C_{12}$ alkyl group; $R^3$ is absent or a $C_1$-$C_{12}$ alkoxy group; $R^4$ is absent or a $C_1$-$C_{12}$ alkoxy group; and $R^5$ is H, a $C_1$-$C_{12}$ alkyl group, or a $C_1$-$C_3$ alkanol. In one embodiment, $R^1$ and $R^2$ are both t-butyl groups.

In one embodiment, the present invention provides a compound having the following formula (VIII):

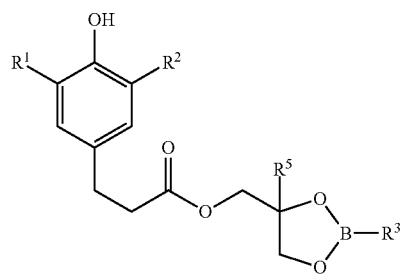

Formula (VIII)

wherein $R^1$ and $R^2$ are each independently a $C_1$-$C_{12}$ alkyl group; $R^3$ is a $C_1$-$C_{12}$ alkoxy group; and $R^5$ is H, a $C_1$-$C_{12}$ alkyl group, or a $C_1$-$C_3$ alkanol. In one embodiment, $R^1$ and $R^2$ are both t-butyl groups. In one embodiment, $R^1$ and $R^2$ are both t-butyl groups.

In one embodiment, the present invention provides a compound having the following formula (IX):

Formula (IX)

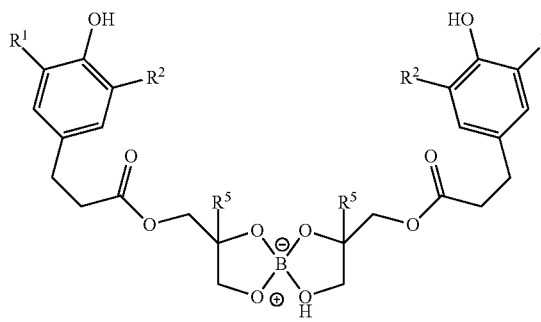

Wherein $R^1$ and $R^2$ are each independently a $C_1$-$C_{12}$ alkyl group and $R^5$ is H, a $C_1$-$C_{12}$ alkyl group, or a $C_1$-$C_3$ alkanol. In one embodiment, $R^1$ and $R^2$ are both t-butyl groups.

In an aspect, the invention provides a lubricating oil composition comprising:
i. a major amount of base oil of lubricating viscosity; and
ii. a compound comprising the reaction product of
  a. a boron containing compound,
  b. a phenolic ester polyol, and
  c. an alcohol.

In an aspect, the invention provides a lubricating oil composition comprising:
i. a major amount of base oil of lubricating viscosity; and
ii. a compound comprising the reaction product of
  a. a boron containing compound, and
  b. a phenolic ester polyol.

In an aspect, the invention provides a lubricating oil composition comprising:
i. a major amount of base oil of lubricating viscosity; and
ii. a compound comprising the reaction product of
  a. a boron containing compound,
  b. a polyol, and
  c. a phenolic acid or ester.

In an aspect, the invention provides a lubricating oil composition comprising: a major amount of base oil of lubricating viscosity; and a compound having the following formula (IV):

Formula (IV)

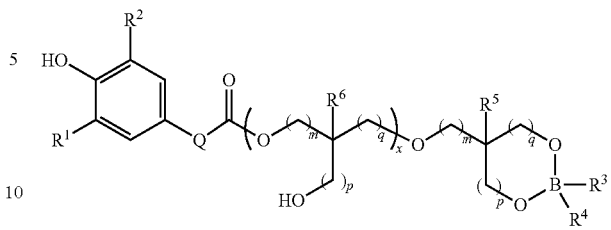

wherein Q is an alkylene group of 2 to 6 carbon atoms; each m is independently 1, 2, or 3; each p is independently 0, 1, 2, or 3; each q is independently 0, 1, 2, or 3; x is 0, 1, or 2; $R^1$ and $R^2$ are each independently a $C_1$-$C_{12}$ alkyl group; $R^3$ is absent or a $C_1$-$C_{12}$ alkoxy group; $R^4$ is absent or a $C_1$-$C_{12}$ alkoxy group; $R^5$ is H, a $C_1$-$C_{12}$ alkyl group, a $C_1$-$C_3$ alkanol; and $R^6$ is H, a $C_1$-$C_{12}$ alkyl group, or a $C_1$-$C_3$ alkanol. In one embodiment, $R^1$ and $R^2$ are both t-butyl groups.

In an aspect, the invention provides a method for operating an internal combustion engine comprising lubricating said engine with a lubricating oil composition comprising: a major amount of base oil of lubricating viscosity; and a compound having the following formula (IV):

Formula (IV)

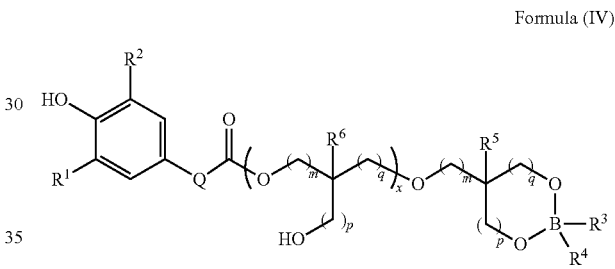

wherein Q is an alkylene group of 2 to 6 carbon atoms; each m is independently 1, 2, or 3; each p is independently 0, 1, 2, or 3; each q is independently 0, 1, 2, or 3; x is 0, 1, or 2; $R^1$ and $R^2$ are each independently a $C_1$-$C_{12}$ alkyl group; $R^3$ is absent or a $C_1$-$C_{12}$ alkoxy group; $R^4$ is absent or a $C_1$-$C_{12}$ alkoxy group; $R^5$ is H, a $C_1$-$C_{12}$ alkyl group, a $C_1$-$C_3$ alkanol; and $R^6$ is H, a $C_1$-$C_{12}$ alkyl group, or a $C_1$-$C_3$ alkanol. In one embodiment, $R^1$ and $R^2$ are both t-butyl groups.

In an aspect, the invention provides a lubricating oil composition comprising: a major amount of base oil of lubricating viscosity; and a compound having the following formula (V):

Formula (V)

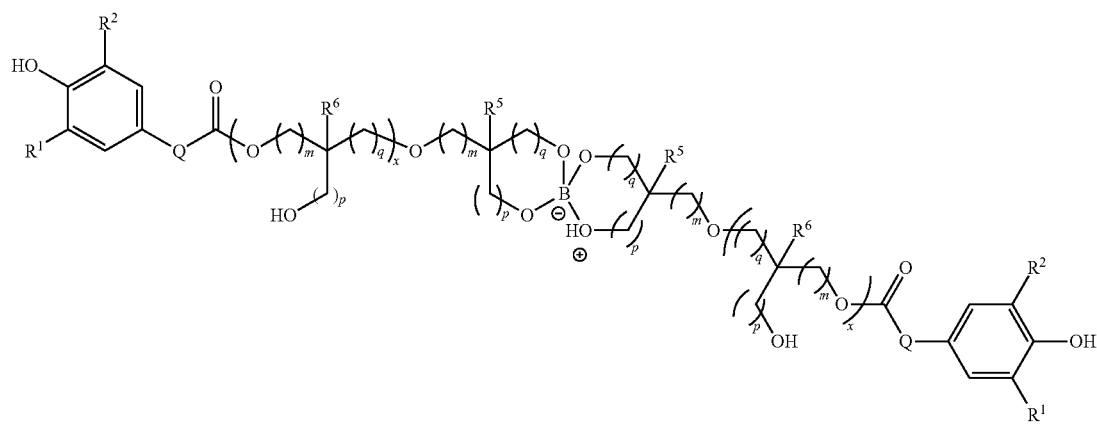

wherein Q is an alkylene group of 2 to 6 carbon atoms; each m is independently 1, 2, or 3; each p is independently 0, 1, 2, or 3; each q is independently 0, 1, 2, or 3; x is 0, 1, or 2; $R^1$ and $R^2$ are each independently a $C_1$-$C_{12}$ alkyl group; $R^5$ is H, a $C_1$-$C_{12}$ alkyl group, or a $C_1$-$C_3$ alkanol; and $R^6$ is H, a $C_1$-$C_{12}$ alkyl group, or a $C_1$-$C_3$ alkanol. In one embodiment, $R^1$ and $R^2$ are both t-butyl groups.

In an aspect, the invention provides a method for operating an internal combustion engine comprising lubricating said engine with a lubricating oil composition comprising: a major amount of base oil of lubricating viscosity; and a compound having the following formula (V):

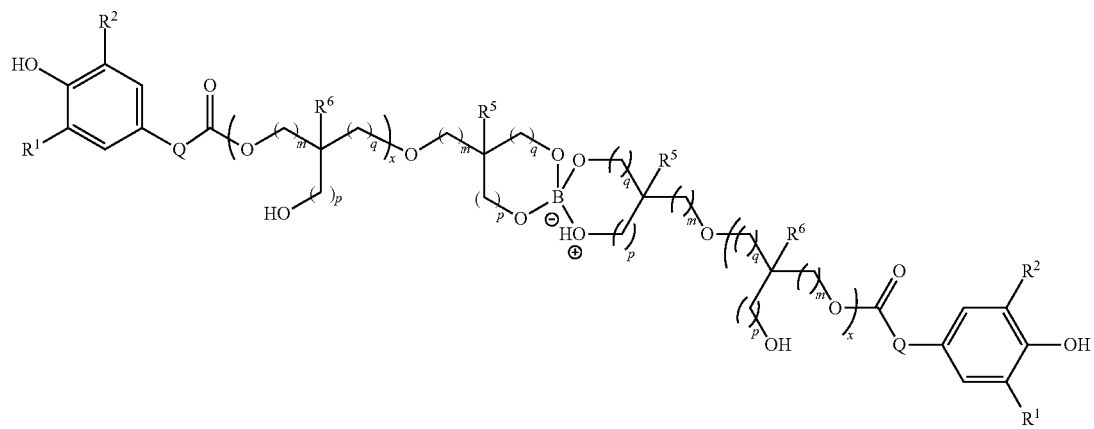

Formula (V)

wherein Q is an alkylene group of 2 to 6 carbon atoms; each m is independently 1, 2, or 3; each p is independently 0, 1, 2, or 3; each q is independently 0, 1, 2, or 3; x is 0, 1, or 2; $R^1$ and $R^2$ are each independently a $C_1$-$C_{12}$ alkyl group; $R^5$ is H, a $C_1$-$C_{12}$ alkyl group, or a $C_1$-$C_3$ alkanol; and $R^6$ is H, a $C_1$-$C_{12}$ alkyl group, or a $C_1$-$C_3$ alkanol. In one embodiment, $R^1$ and $R^2$ are both t-butyl groups.

In an aspect, the present invention provides a process for preparing a borated compound comprising, reacting a boron containing compound, a phenolic ester polyol, and optionally, an alcohol for a time and temperature sufficient to form said borated compound.

The oil soluble/dispersible phenolic ester polyol can be borated by adding the boron reactant (e.g. boric acid) to at least one of the oil soluble/dispersible phenolic ester polyol reactants represented by Formula I; in a suitable reaction vessel and heating the resulting reaction mixture to boronate the oil soluble/dispersible phenolic ester polyol. The reaction temperature is typically conducted at temperatures up to about 250° C., preferably from about 50° C. to about 225° C., and more preferably from about 75° C. to about 150° C. Time for the reaction can be from 2 to 4 hours up to 24 to 48 hours or more, depending upon the temperature; reaction pressure; presence and type of solvents; or presence and type of catalyst. Typically the reaction is conducted under atmospheric pressure however the reaction may be conducted under pressure or vacuum. Furthermore, where conditions warrant it a solvent may be used. In general any relatively non-polar, unreactive solvent may be used, such as benzene, toluene, xylene and 1,4-dioxane or mineral oil. Other hydrocarbon solvents and mixtures may also be employed. Generally the reaction can be carried out without additional solvent.

In an aspect, the present invention provides a process for preparing a borated compound comprising, reacting a boron containing compound, a polyol, and phenolic acid or ester for a time and temperature sufficient to form said borated compound. In an embodiment, the boron containing compound and polyol are reacted in a first step followed by reaction with a phenolic acid or ester to form said borated compound. In one embodiment, the molar ratio of boron containing compound:polyol:phenolic acid or ester is about 1:2:2, thus forming a dimer-like structure. In another embodiment, the molar ratio of boron containing compound:polyol:phenolic acid or ester is about 1:2:1.

The oil soluble/dispersible polyol can be borated by adding the boron reactant (e.g. boric acid) to at least one of the oil soluble/dispersible polyol reactants represented by Formula III; in a suitable reaction vessel and heating the resulting reaction mixture to boronate the oil soluble/dispersible polyol. The reaction temperature to form this borated complex is typically conducted at temperatures up to about 250° C., preferably from about 50° C. to about 225° C., and more preferably from about 75° C. to about 150° C. To this borated complex is added the phenolic acid or ester. The reaction temperature to form the ester is typically conducted at temperatures up to about 250° C., preferably from about 50° C. to about 225° C., and more preferably from about 75° C. to about 150° C. Time for the reaction can be from 2 to 4 hours up to 24 to 48 hours or more, depending upon the temperature; reaction pressure; presence and type of solvents; or presence and type of catalyst. Typically the reaction is conducted under atmospheric pressure however the reaction may be conducted under pressure or vacuum. Furthermore, where conditions warrant it a solvent may be used. In general any relatively non-polar, unreactive solvent may be used, such as benzene, toluene, xylene and 1,4-dioxane or mineral oil. Other hydrocarbon solvents and mixtures may also be employed. Generally the reaction can be carried out without additional solvent.

Typically the reaction is conducted until water ceases to evolve from the reaction mixture indicating completion of the reaction. The removal of this water is facilitated by either by use of an inert gas, such as nitrogen contacting the surface of the reaction mixture or by conducting the reaction at reduced pressure.

In an aspect, the present invention provides a process for preparing a borated compound comprising, reacting a phenolic ester polyol having the formula (I):

Formula (I)

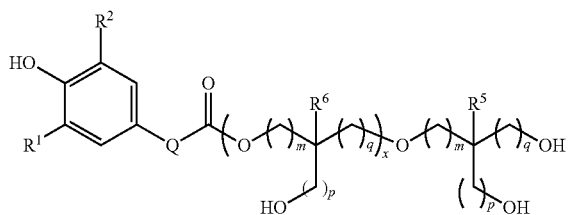

wherein Q is an alkylene group of 2 to 6 carbon atoms; each m is independently 1, 2, or 3; each p is independently 0, 1, 2, or 3; each q is independently 0, 1, 2, or 3; x is 0, 1, or 2; $R^1$ and $R^2$ are each independently a $C_1$-$C_{12}$ alkyl group; $R^5$ is H, a $C_1$-$C_{12}$ alkyl group, or a $C_1$-$C_3$ alkanol; and $R^6$ is H, a $C_1$-$C_{12}$ alkyl group, or a $C_1$-$C_3$ alkanol; a boron containing compound; and an alcohol, for a time and temperature sufficient to form said borated compound. In an embodiment, the ratio of the hindered phenolic ester polyol, boron containing compound and alcohol is about a 1:1:1 molar ratio.

In another aspect, the present invention provides a process for preparing a borated compound comprising, reacting a hindered phenolic ester polyol having the formula (I):

Formula (I)

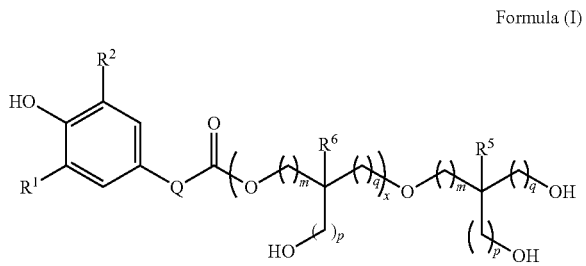

wherein Q is an alkylene group of 2 to 6 carbon atoms; each m is independently 1, 2, or 3; each p is independently 0, 1, 2, or 3; each q is independently 0, 1, 2, or 3; x is 0, 1, or 2; $R^1$ and $R^2$ are each independently a $C_1$-$C_{12}$ alkyl group; $R^5$ is H, a $C_1$-$C_{12}$ alkyl group, or a $C_1$-$C_3$ alkanol; and $R^6$ is H, a $C_1$-$C_{12}$ alkyl group, or a $C_1$-$C_3$ alkanol; and a boron containing compound for a time and temperature sufficient to form said borated compound. Preferably, for every molar equivalent of said boron containing compound there are about two molar equivalents of the phenolic ester polyol, thus forming a dimer-like structure.

In another aspect, the present invention provides a process for preparing a borated compound comprising, reacting a polyol having the formula (III):

(Formula III)

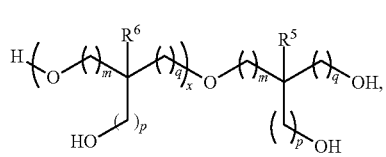

wherein each m is independently 1, 2, or 3; each p is independently 0, 1, 2, or 3; each q is independently 0, 1, 2, or 3; x is 0, 1, or 2; $R^5$ is H, a $C_1$-$C_{12}$ alkyl group, or a $C_1$-$C_3$ alkanol; and $R^6$ is H, a $C_1$-$C_{12}$ alkyl group, or a $C_1$-$C_3$ alkanol; a boron containing compound; and a phenolic acid or ester having the formula (II):

(Formula II)

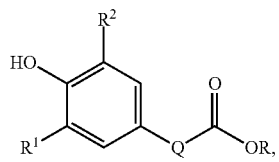

wherein Q is an alkylene group of 2 to 6 carbon atoms; R is H or a moiety suitable to undergo transesterification; $R^1$ and $R^2$ are each independently a $C_1$-$C_{12}$ alkyl group for a time and temperature sufficient to form said borated compound. In one embodiment, the moiety suitable to undergo transesterification is a methyl or ethyl group. In an embodiment, the boron containing compound and polyol are reacted in a first step followed by reaction with a phenolic ester to form said borated compound. In one embodiment, the molar ratio of boron containing compound:polyol:phenolic acid or ester is about 1:2:2, thus forming a dimer-like structure.

The borated compound of the present invention is soluble and/or dispersible in oil. Thus, the borated compound may advantageously be employed in a lubricating oil composition. The oil soluble and/or oil dispersible borated compound is a multifunctional additive in that when employed as an additive in lubricating oils, it provides reduced frictional characteristics and also imparts anti-oxidancy characteristics.

Generally, the lubricating oil soluble additive concentrates of the invention are further blended with additional lubricant base oil stocks and/or additional additives/additive concentrates to provide a finished lubricant. It is desired that the carrier liquid solubilizes or disperses the lubricating oil soluble additive of the invention and provides an additive concentrate that can be blended into additional lubricant base oil. The present invention therefore further provides an additive concentrate composition comprising an inert carrier fluid and from 2.0% to 90% by weight, based on the total concentrate, of a lubricant additive composition according to the invention. The inert carrier fluid may be a lubricating oil or a suitable hydrocarbon solvent.

These concentrates usually contain from about 2.0% to about 90% by weight, preferably 10% to 50% by weight of the additive composition of this invention and may contain, in addition, one or more other additives known in the art and described below. The remainder of the concentrate is the substantially inert carrier liquid or suitable hydrocarbon solvent.

For finished lubricants, typically the amount of borated oil soluble/dispersible compound will be from about 0.001 wt % to about 10 wt % based upon the total weight of the lubricating oil composition. Preferably the oil soluble/dispersible borated compound is employed in an amount from 0.05 wt % to about 5 wt % and even more preferably from about 0.1 wt % to 1.5 wt % based upon the total weight of the lubricating oil composition.

The lubricating oil compositions of this invention can be used in the lubrication of essentially any internal combustion engine, including automobile and truck engines, two cycle engines, diesel engines, aviation piston engines, marine and railroad engines and the like. Also contemplated are lubricating oils for gas fired engines, alcohol (e.g. methanol)

powered engines, stationery powered engines, industrial engines, turbines, hydraulic systems, transmissions, gears and the like. Particularly useful are heavy duty diesel engines wherein said lubricating oil compositions of this invention can be employed to improve fuel economy and wherein the oil soluble/dispersible borated compound may provide an antioxidant/friction modifying benefit to the lubricating oil composition.

The lubricating oil composition disclosed herein is used to lubricate an internal combustion engine such as a spark ignition engine, or a compression ignition diesel engine, e.g., a heavy duty diesel engine or a compression ignition diesel engine equipped with at least one of an exhaust gas recirculation (EGR) system; a catalytic converter; and a particulate trap. Such a motor oil composition may be used to lubricate all major moving parts in any reciprocating internal combustion engine, reciprocating compressors and in steam engines of crankcase design. In automotive applications, the motor oil composition may also be used to cool hot engine parts, keep the engine free of rust and deposits, and seal the rings and valves against leakage of combustion gases.

If desired, other additives known in the art may be added to the lubricating oil basestock. Such additives include dispersants, detergents, antiwear agents, extreme pressure agents, antioxidants, rust inhibitors, corrosion inhibitors, pour point depressants, viscosity index improvers, other friction modifiers and the like. Not limiting examples of such are herein below.

The Oil of Lubricating Viscosity

The lubricating oil compositions disclosed herein generally comprise at least one oil of lubricating viscosity. Any base oil known to a skilled artisan can be used as the oil of lubricating viscosity disclosed herein. Some base oils suitable for preparing the lubricating oil compositions have been described in Mortier et al., "*Chemistry and Technology of Lubricants,*" 3rd Edition, London, Springer, Chapters 1 and 2 (2011); and A. Sequeria, Jr., "*Lubricant Base Oil and Wax Processing,*" New York, Marcel Decker, Chapter 6, (1994); and D. V. Brock, *Lubrication Engineering*, Vol. 43, pages 184-5, (1987), all of which are incorporated herein by reference. Generally, the amount of the base oil in the lubricating oil composition may be from about 70 to about 99.5 wt. %, based on the total weight of the lubricating oil composition. In some embodiments, the amount of the base oil in the lubricating oil composition is from about 75 to about 99 wt. %, from about 80 to about 98.5 wt. %, or from about 80 to about 98 wt. %, based on the total weight of the lubricating oil composition.

In certain embodiments, the base oil is or comprises any natural or synthetic lubricating base oil fraction. Some non-limiting examples of synthetic oils include oils, such as polyalphaolefins or PAOs, prepared from the polymerization of at least one alpha-olefin, such as ethylene; and oils or from hydrocarbon synthesis procedures using carbon monoxide and hydrogen gases, such as the Fisher-Tropsch process. In certain embodiments, the base oil comprises less than about 10 wt. % of one or more heavy fractions, based on the total weight of the base oil. A heavy fraction refers to a lube oil fraction having a viscosity of at least about 20 cSt at 100° C. In certain embodiments, the heavy fraction has a viscosity of at least about 25 cSt or at least about 30 cSt at 100° C. In further embodiments, the amount of the one or more heavy fractions in the base oil is less than about 10 wt. %, less than about 5 wt. %, less than about 2.5 wt. %, less than about 1 wt. %, or less than about 0.1 wt. %, based on the total weight of the base oil. In still further embodiments, the base oil comprises no heavy fraction.

In certain embodiments, the lubricating oil compositions comprise a major amount of a base oil of lubricating viscosity. In some embodiments, the base oil has a kinematic viscosity at 100° C. from about 2.5 centistokes (cSt) to about 20 cSt. The kinematic viscosity of the base oils or the lubricating oil compositions disclosed herein can be measured according to ASTM D 445, which is incorporated herein by reference.

In other embodiments, the base oil is or comprises a base stock or blend of base stocks. In further embodiments, the base stocks are manufactured using a variety of different processes including, but not limited to, distillation, solvent refining, hydrogen processing, oligomerization, esterification, and rerefining. In some embodiments, the base stocks comprise a rerefined stock. In further embodiments, the rerefined stock shall be substantially free from materials introduced through manufacturing, contamination, or previous use.

In some embodiments, the base oil comprises one or more of the base stocks in one or more of Groups I-V as specified in the American Petroleum Institute (API) Publication 1509, Seventeenth Edition, September 2012 (i.e., API Base Oil Interchangeability Guidelines for Passenger Car Motor Oils and Diesel Engine Oils), which is incorporated herein by reference. The API guideline defines a base stock as a lubricant component that may be manufactured using a variety of different processes. Groups I, II and III base stocks are mineral oils, each with specific ranges of the amount of saturates, sulfur content and viscosity index. Group IV base stocks are polyalphaolefins (PAO). Group V base stocks include all other base stocks not included in Group I, II, III, or IV.

The saturates levels, sulfur levels and viscosity indices for Group I, II and III base stocks are listed in Table 1 below.

TABLE 1

| Group | Saturates (As determined by ASTM D 2007) | Sulfur (As determined by ASTM D 2270) | Viscosity Index (As determined by ASTM D 4294, ASTM D 4297 or ASTM D 3120) |
| --- | --- | --- | --- |
| I | Less than 90% saturates. | Greater than or equal to 0.03% sulfur. | Greater than or equal to 80 and less than 120. |
| II | Greater than or equal to 90% saturates. | Less than 0.03% sulfur. | Greater than or equal to 80 and less than 120. |
| III | Greater than or equal to 90% saturates. | Less than or equal to 0.03% sulfur. | Greater than or equal to 120. |

In some embodiments, the base oil comprises one or more of the base stocks in Group I, II, III, IV, V or a combination thereof. In other embodiments, the base oil comprises one or more of the base stocks in Group II, III, IV or a combination thereof.

The base oil may be selected from the group consisting of natural oils of lubricating viscosity, synthetic oils of lubricating viscosity and mixtures thereof. In some embodiments, the base oil includes base stocks obtained by isomerization of synthetic wax and slack wax, as well as hydrocrackate base stocks produced by hydrocracking (in addition to or instead of solvent extracting) the aromatic and polar components of the crude. In other embodiments, the base oil of lubricating viscosity includes natural oils, such as animal oils, vegetable oils, mineral oils, oils derived from coal or shale, and combinations thereof. Some non-limiting examples of animal oils include bone oil, lanolin, fish oil, lard oil, dolphin oil, seal oil, shark oil, tallow oil, and whale oil. Some non-limiting examples of vegetable oils include castor oil, olive oil, peanut oil, rapeseed oil, corn oil, sesame oil, cottonseed oil, soybean oil, sunflower oil, safflower oil, hemp oil, linseed oil, tung oil, oiticica oil, jojoba oil, and meadow foam oil. Such oils may be partially or fully hydrogenated. Some non-limiting examples of mineral oils include Groups I, II, and III base stocks, liquid petroleum oils and solvent treated or acid-treated mineral oils of the paraffinic, naphthenic or mixed paraffinic-naphthenic types. In some embodiments, the mineral oils are neat or low viscosity mineral oils.

In some embodiments, the synthetic oils of lubricating viscosity include hydrocarbon oils and halo-substituted hydrocarbon oils such as polymerized and inter-polymerized olefins, alkylbenzenes, polyphenyls, alkylated diphenyl ethers, alkylated diphenyl sulfides, as well as their derivatives, analogues and homologues thereof, and the like. In other embodiments, the synthetic oils include alkylene oxide polymers, interpolymers, copolymers and derivatives thereof wherein the terminal hydroxyl groups can be modified by esterification, etherification, and the like. In further embodiments, the synthetic oils include the esters of dicarboxylic acids with a variety of alcohols. In certain embodiments, the synthetic oils include esters made from $C_5$ to $C_{12}$ monocarboxylic acids and polyols and polyol ethers. In further embodiments, the synthetic oils include tri-alkyl phosphate ester oils, such as tri-n-butyl phosphate and tri-iso-butyl phosphate.

In some embodiments, the synthetic oils of lubricating viscosity include silicon-based oils (such as the polyalkyl-, polyaryl-, polyalkoxy-, polyaryloxy-siloxane oils and silicate oils). In other embodiments, the synthetic oils include liquid esters of phosphorus-containing acids, polymeric tetrahydrofurans, polyalphaolefins, and the like.

Base oil derived from the hydroisomerization of wax may also be used, either alone or in combination with the aforesaid natural and/or synthetic base oil. Such wax isomerate oil is produced by the hydroisomerization of natural or synthetic waxes or mixtures thereof over a hydroisomerization catalyst.

In further embodiments, the base oil comprises a poly-alpha-olefin (PAO). In general, the poly-alpha-olefins may be derived from an alpha-olefin having from about 2 to about 30, from about 4 to about 20, or from about 6 to about 16 carbon atoms. Non-limiting examples of suitable poly-alpha-olefins include those derived from octene, decene, mixtures thereof, and the like. These poly-alpha-olefins may have a viscosity from about 2 to about 15, from about 3 to about 12, or from about 4 to about 8 centistokes at 100° C. In some instances, the poly-alpha-olefins may be used together with other base oils such as mineral oils.

In further embodiments, the base oil comprises a polyalkylene glycol or a polyalkylene glycol derivative, where the terminal hydroxyl groups of the polyalkylene glycol may be modified by esterification, etherification, acetylation and the like. Non-limiting examples of suitable polyalkylene glycols include polyethylene glycol, polypropylene glycol, polyisopropylene glycol, and combinations thereof. Non-limiting examples of suitable polyalkylene glycol derivatives include ethers of polyalkylene glycols (e.g., methyl ether of polyisopropylene glycol, diphenyl ether of polyethylene glycol, diethyl ether of polypropylene glycol, etc.), mono- and polycarboxylic esters of polyalkylene glycols, and combinations thereof. In some instances, the polyalkylene glycol or polyalkylene glycol derivative may be used together with other base oils such as poly-alpha-olefins and mineral oils.

In further embodiments, the base oil comprises any of the esters of dicarboxylic acids (e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, alkenyl malonic acids, and the like) with a variety of alcohols (e.g., butyl alcohol, hexyl alcohol, dodecyl alcohol, 2-ethylhexyl alcohol, ethylene glycol, diethylene glycol monoether, propylene glycol, and the like). Non-limiting examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the like.

In further embodiments, the base oil comprises a hydrocarbon prepared by the Fischer-Tropsch process. The Fischer-Tropsch process prepares hydrocarbons from gases containing hydrogen and carbon monoxide using a Fischer-Tropsch catalyst. These hydrocarbons may require further processing in order to be useful as base oils. For example, the hydrocarbons may be dewaxed, hydroisomerized, and/or hydrocracked using processes known to a person of ordinary skill in the art.

In further embodiments, the base oil comprises an unrefined oil, a refined oil, a rerefined oil, or a mixture thereof. Unrefined oils are those obtained directly from a natural or synthetic source without further purification treatment. Non-limiting examples of unrefined oils include shale oils obtained directly from retorting operations, petroleum oils obtained directly from primary distillation, and ester oils obtained directly from an esterification process and used without further treatment. Refined oils are similar to the unrefined oils except the former have been further treated by one or more purification processes to improve one or more properties. Many such purification processes are known to those skilled in the art such as solvent extraction, secondary distillation, acid or base extraction, filtration, percolation, and the like. Rerefined oils are obtained by applying to refined oils processes similar to those used to obtain refined oils. Such rerefined oils are also known as reclaimed or reprocessed oils and often are additionally treated by processes directed to removal of spent additives and oil breakdown products.

Additional Lubricating Oil Additives

The lubricating oil compositions of the present invention may also contain other conventional additives that can impart or improve any desirable property of the lubricating oil composition in which these additives are dispersed or dissolved. Any additive known to a person of ordinary skill in the art may be used in the lubricating oil compositions disclosed herein. Some suitable additives have been described in Mortier et al., "Chemistry and Technology of Lubricants", 2nd Edition, London, Springer, (1996); and Leslie R. Rudnick, "Lubricant Additives: Chemistry and Applications", New York, Marcel Dekker (2003), both of which are incorporated herein by reference. For example, the lubricating oil compositions can be blended with antioxidants, anti-wear agents, detergents such as metal detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and the like and mixtures thereof. A variety of the additives are known and commercially available. These additives, or their analogous compounds, can be employed for the preparation of the lubricating oil compositions of the invention by the usual blending procedures.

In general, the concentration of each of the additives in the lubricating oil composition, when used, may range from about 0.001 wt. % to about 20 wt. %, from about 0.01 wt. % to about 15 wt. %, or from about 0.1 wt. % to about 10 wt. %, based on the total weight of the lubricating oil composition.

Ashless Dispersant

The lubricating oil compositions can contain one or more ashless dispersants containing one or more basic nitrogen atoms. The basic nitrogen compound for use herein must contain basic nitrogen as measured, for example, by ASTM D664 test or D2896. The basic nitrogen compounds are selected from the group consisting of succinimides, polysuccinimides, carboxylic acid amides, hydrocarbyl monoamines, hydrocarbon polyamines, Mannich bases, phosphoramides, thiophosphoramides, phosphonamides, dispersant viscosity index improvers, and mixtures thereof. These basic nitrogen-containing compounds are described below (keeping in mind the reservation that each must have at least one basic nitrogen). Any of the nitrogen-containing compositions may be post-treated with, e.g., boron or ethylene carbonate, using procedures well known in the art so long as the compositions continue to contain basic nitrogen.

Another class of nitrogen-containing compositions useful in preparing the dispersants employed in this invention includes the so-called dispersant viscosity index improvers (VI improvers). These VI improvers are commonly prepared by functionalizing a hydrocarbon polymer, especially a polymer derived from ethylene and/or propylene, optionally containing additional units derived from one or more co-monomers such as alicyclic or aliphatic olefins or diolefins. The functionalization may be carried out by a variety of processes which introduce a reactive site or sites which usually has at least one oxygen atom on the polymer. The polymer is then contacted with a nitrogen-containing source to introduce nitrogen-containing functional groups on the polymer backbone. Commonly used nitrogen sources include any basic nitrogen compound especially those nitrogen-containing compounds and compositions described herein. Preferred nitrogen sources are alkylene amines, such as ethylene amines, alkyl amines, and Mannich bases.

In one embodiment, the basic nitrogen compounds for use in making the dispersants are succinimides, carboxylic acid amides, and Mannich bases. In another preferred embodiment, the basic nitrogen compounds for use in making the dispersants are succinimides having an average molecular weight of about 1000 or about 1300 or about 2300 and mixtures thereof. Such succinimides can be post treated with boron or ethylene carbonate as known in the art.

Generally, the amount of the one or more dispersants in the lubricating oil composition will vary from about 0.05 to about 15 wt. %, based on the total weight of the lubricating oil composition. In another embodiment, the amount of the one or more dispersants will vary from about 0.1 to about 10 wt. %, based on the total weight of the lubricating oil composition.

Antioxidants

In addition to the antioxidant of the present invention, the lubricating oil composition of the can contain one or more additional antioxidants that can reduce or prevent the oxidation of the base oil. Any antioxidant known by a person of ordinary skill in the art may be used in the lubricating oil composition. Non-limiting examples of suitable antioxidants include amine-based antioxidants (e.g., alkyl diphenylamines such as bis-nonylated diphenylamine, bis-octylated diphenylamine, and octylated/butylated diphenylamine, phenyl-α-naphthylamine, alkyl or arylalkyl substituted phenyl-α-naphthylamine, alkylated p-phenylene diamines, tetramethyl-diaminodiphenylamine and the like), phenolic antioxidants (e.g., 2-tert-butylphenol, 4-methyl-2,6-di-tert-butylphenol, 2,4,6-tri-tert-butylphenol, 2,6-di-tert-butyl-p-cresol, 2,6-di-tert-butylphenol, 4,4'-methylenebis-(2,6-di-tert-butylphenol), 4,4'-thiobis(6-di-tert-butyl-o-cresol) and the like), sulfur-based antioxidants (e.g., dilauryl-3,3'-thiodipropionate, sulfurized phenolic antioxidants and the like), phosphorous-based antioxidants (e.g., phosphites and the like), zinc dithiophosphate, oil-soluble copper compounds and combinations thereof. The amount of the antioxidant may vary from about 0.01 wt. % to about 10 wt. %, from about 0.05 wt. % to about 5 wt. %, or from about 0.1 wt. % to about 3 wt. %, based on the total weight of the lubricating oil composition.

Detergents

The lubricating oil composition of the present invention can contain a detergent. Metal-containing or ash-forming detergents function as both detergents to reduce or remove deposits and as acid neutralizers or rust inhibitors, thereby reducing wear and corrosion and extending engine life. Detergents generally comprise a polar head with a long hydrophobic tail. The polar head comprises a metal salt of an acidic organic compound. The salts may contain a substantially stoichiometric amount of the metal in which case they are usually described as normal or neutral salts. A large amount of a metal base may be incorporated by reacting excess metal compound (e.g., an oxide or hydroxide) with an acidic gas (e.g., carbon dioxide).

Detergents that may be used include oil-soluble neutral and overbased sulfonates, borated sulfonates, phenates, sulfurized phenates, thiophosphonates, salicylates, and naphthenates and other oil-soluble carboxylates of a metal, particularly the alkali or alkaline earth metals, e.g., barium, sodium, potassium, lithium, calcium, and magnesium. The most commonly used metals are calcium and magnesium, which may both be present in detergents used in a lubricant, and mixtures of calcium and/or magnesium with sodium.

Generally, the amount of the additional detergent can be from about 0.001 wt. % to about 25 wt. %, from about 0.05 wt. % to about 20 wt. %, or from about 0.1 wt. % to about 15 wt. %, based on the total weight of the lubricating oil composition.

Friction Modifiers

In addition to the friction modifier of the present invention, the lubricating oil composition of the present invention can contain additional friction modifiers that can lower the friction between moving parts. Any friction modifier known by a person of ordinary skill in the art may be used in the lubricating oil composition. Non-limiting examples of suitable friction modifiers include fatty carboxylic acids; derivatives (e.g., alcohol, esters, borated esters, amides, metal salts and the like) of fatty carboxylic acid; mono-, di- or tri-alkyl substituted phosphoric acids or phosphonic acids; derivatives (e.g., esters, amides, metal salts and the like) of mono-, di- or tri-alkyl substituted phosphoric acids or phosphonic acids; mono-, di- or tri-alkyl substituted amines; mono- or di-alkyl substituted amides and combinations thereof. In some embodiments examples of friction modifiers include, but are not limited to, alkoxylated fatty amines; borated fatty epoxides; fatty phosphites, fatty epoxides, fatty amines, borated alkoxylated fatty amines, metal salts of fatty acids, fatty acid amides, glycerol esters, borated glycerol esters; and fatty imidazolines as disclosed in U.S. Pat. No. 6,372,696, the contents of which are incorporated by reference herein; friction modifiers obtained from a reaction product of a $C_4$ to $C_{75}$, or a $C_6$ to $C_{24}$, or a $C_6$ to $C_{20}$, fatty acid ester and a nitrogen-containing compound selected from the group consisting of ammonia, and an alkanolamine and the like and mixtures thereof. The amount of the friction modifier may vary from about 0.01 wt. % to about 10 wt. %, from about 0.05 wt. % to about 5 wt. %, or from about 0.1 wt. % to about 3 wt. %, based on the total weight of the lubricating oil composition.

Antiwear Compounds

The lubricating oil composition of the present invention can contain one or more anti-wear agents that can reduce friction and excessive wear. Any anti-wear agent known by a person of ordinary skill in the art may be used in the lubricating oil composition. Non-limiting examples of suitable anti-wear agents include zinc dithiophosphate, metal (e.g., Pb, Sb, Mo and the like) salts of dithiophosphates, metal (e.g., Zn, Pb, Sb, Mo and the like) salts of dithiocarbamates, metal (e.g., Zn, Pb, Sb and the like) salts of fatty acids, boron compounds, phosphate esters, phosphite esters, amine salts of phosphoric acid esters or thiophosphoric acid esters, reaction products of dicyclopentadiene and thiophosphoric acids and combinations thereof. The amount of the anti-wear agent may vary from about 0.01 wt. % to about 5 wt. %, from about 0.05 wt. % to about 3 wt. %, or from about 0.1 wt. % to about 1 wt. %, based on the total weight of the lubricating oil composition.

In certain embodiments, the anti-wear agent is or comprises a dihydrocarbyl dithiophosphate metal salt, such as zinc dialkyl dithiophosphate compounds. The metal of the dihydrocarbyl dithiophosphate metal salt may be an alkali or alkaline earth metal, or aluminum, lead, tin, molybdenum, manganese, nickel or copper. In some embodiments, the metal is zinc. In other embodiments, the alkyl group of the dihydrocarbyl dithiophosphate metal salt has from about 3 to about 22 carbon atoms, from about 3 to about 18 carbon atoms, from about 3 to about 12 carbon atoms, or from about 3 to about 8 carbon atoms. In further embodiments, the alkyl group is linear or branched.

The amount of the dihydrocarbyl dithiophosphate metal salt including the zinc dialkyl dithiophosphate salts in the lubricating oil composition disclosed herein is measured by its phosphorus content. In some embodiments, the phosphorus content of the lubricating oil composition disclosed herein is from about 0.01 wt. % to about 0.14 wt., based on the total weight of the lubricating oil composition.

Foam Inhibitors

The lubricating oil composition of the present invention can contain one or more foam inhibitors or anti-foam inhibitors that can break up foams in oils. Any foam inhibitor or anti-foam known by a person of ordinary skill in the art may be used in the lubricating oil composition. Non-limiting examples of suitable foam inhibitors or anti-foam inhibitors include silicone oils or polydimethylsiloxanes, fluorosilicones, alkoxylated aliphatic acids, polyethers (e.g., polyethylene glycols), branched polyvinyl ethers, alkyl acrylate polymers, alkyl methacrylate polymers, polyalkoxyamines and combinations thereof. In some embodiments, the foam inhibitors or anti-foam inhibitors comprises glycerol monostearate, polyglycol palmitate, a trialkyl monothiophosphate, an ester of sulfonated ricinoleic acid, benzoylacetone, methyl salicylate, glycerol monooleate, or glycerol dioleate. The amount of the foam inhibitors or anti-foam inhibitors may vary from about 0.001 wt. % to about 5 wt. %, from about 0.05 wt. % to about 3 wt. %, or from about 0.1 wt. % to about 1 wt. %, based on the total weight of the lubricating oil composition.

Pour Point Depressants

The lubricating oil composition of the present invention can contain one or more pour point depressants that can lower the pour point of the lubricating oil composition. Any pour point depressant known by a person of ordinary skill in the art may be used in the lubricating oil composition. Non-limiting examples of suitable pour point depressants include polymethacrylates, alkyl acrylate polymers, alkyl methacrylate polymers, di(tetra-paraffin phenol)phthalate, condensates of tetra-paraffin phenol, condensates of a chlorinated paraffin with naphthalene and combinations thereof. In some embodiments, the pour point depressant comprises an ethylene-vinyl acetate copolymer, a condensate of chlorinated paraffin and phenol, polyalkyl styrene or the like. The amount of the pour point depressant may vary from about 0.01 wt. % to about 10 wt. %, from about 0.05 wt. % to about 5 wt. %, or from about 0.1 wt. % to about 3 wt. %, based on the total weight of the lubricating oil composition.

Demulsifiers

In one embodiment, the lubricating oil composition of the present invention does not contain one or more demulsifiers. In another embodiment, the lubricating oil composition of the present invention can contain one or more demulsifiers that can promote oil-water separation in lubricating oil compositions that are exposed to water or steam. Any demulsifier known by a person of ordinary skill in the art may be used in the lubricating oil composition. Non-limiting examples of suitable demulsifiers include anionic surfactants (e.g., alkyl-naphthalene sulfonates, alkyl benzene sulfonates and the like), nonionic alkoxylated alkyl phenol resins, polymers of alkylene oxides (e.g., polyethylene oxide, polypropylene oxide, block copolymers of ethylene oxide, propylene oxide and the like), esters of oil soluble acids, polyoxyethylene sorbitan ester and combinations thereof. The amount of the demulsifier may vary from about 0.01 wt. % to about 10 wt. %, from about 0.05 wt. % to about 5 wt. %, or from about 0.1 wt. % to about 3 wt. %, based on the total weight of the lubricating oil composition.

Corrosion Inhibitors

The lubricating oil composition of the present invention can contain one or more corrosion inhibitors that can reduce corrosion. Any corrosion inhibitor known by a person of ordinary skill in the art may be used in the lubricating oil composition. Non-limiting examples of suitable corrosion inhibitor include half esters or amides of dodecylsuccinic acid, phosphate esters, thiophosphates, alkyl imidazolines, sarcosines and combinations thereof. The amount of the corrosion inhibitor may vary from about 0.01 wt. % to about 5 wt. %, from about 0.05 wt. % to about 3 wt. %, or from about 0.1 wt. % to about 1 wt. %, based on the total weight of the lubricating oil composition.

Extreme Pressure Agents

The lubricating oil composition of the present invention can contain one or more extreme pressure (EP) agents that can prevent sliding metal surfaces from seizing under conditions of extreme pressure. Any extreme pressure agent known by a person of ordinary skill in the art may be used in the lubricating oil composition. Generally, the extreme pressure agent is a compound that can combine chemically with a metal to form a surface film that prevents the welding of asperities in opposing metal surfaces under high loads. Non-limiting examples of suitable extreme pressure agents include sulfurized animal or vegetable fats or oils, sulfurized animal or vegetable fatty acid esters, fully or partially esterified esters of trivalent or pentavalent acids of phosphorus, sulfurized olefins, dihydrocarbyl polysulfides, sulfurized Diels-Alder adducts, sulfurized dicyclopentadiene, sulfurized or co-sulfurized mixtures of fatty acid esters and monounsaturated olefins, co-sulfurized blends of fatty acid, fatty acid ester and alpha-olefin, functionally-substituted dihydrocarbyl polysulfides, thia-aldehydes, thia-ketones, epithio compounds, sulfur-containing acetal derivatives, co-sulfurized blends of terpene and acyclic olefins, and polysulfide olefin products, amine salts of phosphoric acid esters or thiophosphoric acid esters and combinations thereof. The amount of the extreme pressure agent may vary from about 0.01 wt. % to about 5 wt. %, from about 0.05 wt. % to about 3 wt. %, or from about 0.1 wt. % to about 1 wt. %, based on the total weight of the lubricating oil composition.

Rust Inhibitors

The lubricating oil composition of the present invention can contain one or more rust inhibitors that can inhibit the corrosion of ferrous metal surfaces. Any rust inhibitor known by a person of ordinary skill in the art may be used in the lubricating oil composition. Non-limiting examples of suitable rust inhibitors include nonionic polyoxyalkylene agents, e.g., polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate; stearic acid and other fatty acids; dicarboxylic acids; metal soaps; fatty acid amine salts; metal salts of heavy sulfonic acid; partial carboxylic acid ester of polyhydric alcohol; phosphoric esters; (short-chain) alkenyl succinic acids; partial esters thereof and nitrogen-containing derivatives thereof; synthetic alkarylsulfonates, e.g., metal dinonylnaphthalene sulfonates; and the like and mixtures thereof. The amount of the rust inhibitor may vary from about 0.01 wt. % to about 10 wt. %, from about 0.05 wt. % to about 5 wt. %, or from about 0.1 wt. % to about 3 wt. %, based on the total weight of the lubricating oil composition.

Multifunctional Additives

The lubricating oil composition of the present invention can contain one or more multifunctional additives. Non-limiting examples of suitable multifunctional additives include sulfurized oxymolybdenum dithiocarbamate, sulfurized oxymolybdenum organophosphorodithioate, oxymolybdenum monoglyceride, oxymolybdenum diethylate amide, amine-molybdenum complex compound, and sulfur-containing molybdenum complex compound.

Viscosity Index Improvers

The lubricating oil composition of the present invention can contain one or more viscosity index improvers. Non-limiting examples of suitable viscosity index improvers include, but are not limited to, olefin copolymers, such as ethylene-propylene copolymers, styrene-isoprene copolymers, hydrated styrene-isoprene copolymers, polybutene, polyisobutylene, polymethacrylates, vinylpyrrolidone and methacrylate copolymers and dispersant type viscosity index improvers. These viscosity modifiers can optionally be grafted with grafting materials such as, for example, maleic anhydride, and the grafted material can be reacted with, for example, amines, amides, nitrogen-containing heterocyclic compounds or alcohol, to form multifunctional viscosity modifiers (dispersant-viscosity modifiers). Other examples of viscosity modifiers include star polymers (e.g., a star polymer comprising isoprene/styrene/isoprene tri-block). Yet other examples of viscosity modifiers include poly alkyl(meth)acrylates of low Brookfield viscosity and high shear stability, functionalized poly alkyl(meth)acrylates with dispersant properties of high Brookfield viscosity and high shear stability, polyisobutylene having a weight average molecular weight ranging from 700 to 2,500 Daltons and mixtures thereof. The amount of the viscosity index improvers may vary from about 0.01 wt. % to about 25 wt. %, from about 0.05 wt. % to about 20 wt. %, or from about 0.3 wt. % to about 15 wt. %, based on the total weight of the lubricating oil composition.

Metal Deactivators

The lubricating oil composition of the present invention can contain one or more metal deactivators. Non-limiting examples of suitable metal deactivators include disalicylidene propylenediamine, triazole derivatives, thiadiazole derivatives, and mercaptobenzimidazoles.

Each of the foregoing additives, when used, is used at a functionally effective amount to impart the desired properties to the lubricant. Thus, for example, if an additive is a friction modifier, a functionally effective amount of this friction modifier would be an amount sufficient to impart the desired friction modifying characteristics to the lubricant. Generally, the concentration of each of these additives, when used, may range, unless otherwise specified, from about 0.001 wt. % to about 10 wt. %, in one embodiment from about 0.005 wt. % to about 5 wt. %, or in one embodiment from about 0.1 wt. % to about 2.5 wt. %, based on the total weight of the lubricating oil composition. Further, the total amount of the additives in the lubricating oil composition may range from about 0.001 wt. % to about 20 wt. %, from about 0.01 wt. % to about 10 wt. %, or from about 0.1 wt. % to about 5 wt. %, based on the total weight of the lubricating oil composition.

The following examples are presented to exemplify embodiments of the invention but are not intended to limit the invention to the specific embodiments set forth. Unless indicated to the contrary, all parts and percentages are by weight. All numerical values are approximate. When numerical ranges are given, it should be understood that embodiments outside the stated ranges may still fall within the scope of the invention. Specific details described in each example should not be construed as necessary features of the invention.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

EXAMPLES

The following examples are intended for illustrative purposes only and do not limit in any way the scope of the present invention.

Example 1

Example Procedure (Preparation of 2,3-dihydroxypropyl 3-(3,5-di-tert-butyl-4-hydroxyphenyl)propanoate)

To a 1 L reactor fitted with a Deane-Stark trap was added 153.1 g (550 mmol, 1.0 eq) of 3-(3,5-di-tert-butyl-4-hydroxyphenyl)propionic acid and 506.55 g (5.50 mol, 10 eq) of glycerol. Reaction mixture was stirred under a weak nitrogen stream while heated at 160° C. for 24 hours. Product was diluted with water, and then extracted with ethyl acetate and then the organic phase was dried with sodium sulfate. The organic phase was filtered off drying agent and the ethyl acetate was removed by rotary evaporation to reveal clear amber viscous liquid (93% yield by mass).

Example 2

Example Procedure (Preparation of (2-((2-ethylhexyl)oxy)-1,3,2-dioxaborolan-4-yl)methyl 3-(3,5-di-tert-butyl-4-hydroxyphenyl)propanoate)

To a 250 mL reactor fitted with a Deane-Stark trap was added 38.5 g (105.8 mmol, 1.1 eq) of Example 1, 5.95 g (96.2 mmol, 1.0 eq) of boric acid, 12.53 g (96.2 mmol, 1.0 eq) 2-ethylhexanol, and 65 mL toluene. Reaction mixture was stirred under a weak nitrogen stream while heated at 95° C. for 1 hour before raising the temperature to 115° C. with vacuum for 2-3 hours.

Example 3

Example Procedure (Preparation of 3,7-bis(((3-(3,5-d-tert-butyl-4-hydroxyphenyl)propanoyl)oxy)methyl)-1,4,6,9-tetraoxa-5-boraspiro[4,4]nonan-1-ium-5-uide)

To a 250 mL reactor fitted with a Deane-Stark trap was added 96.4 g (232 mmol, 2.2 eq) of Example 1, 6.53 g (106 mmol, 1.0 eq) of boric acid, and 100 mL toluene. Reaction mixture was stirred under a weak nitrogen stream while heated at 95° C. for 1 hour before raising the temperature to 115° C. with house vacuum for 2-3 hours.

Example 4

Example Procedure (Preparation of 3-hydroxy-2-(hydroxymethyl)-2-methylpropyl 3-(3,5-di-tert-butyl-4-hydroxyphenyl)propanoate)

To a 50 mL round bottom flask with a stir bar was added 5.00 g (17.1 mmol, 1.0 eq) of methyl 3-(3,5-di-tert-butyl-4-hydroxyphenyl)propanoate, 10.0 g (83.9 mmol, 4.4 eq) of 2-(hydroxymethyl)-2-methylpropane-1,3-diol, 15 mL toluene, and 7 mL dimethylformamide. A condenser was attached and the reaction mixture was stirred and heated under nitrogen using an oil bath at 100° C. for 24 hours before attaching a Deane-Stark trap and stirring the mixture at 140° C. for 5 hours. The reaction solution was then stirred for 20 hours at 145° C. and then 20 hours at 160° C. with light vacuum. Product was extracted with ethyl acetate, mixture was dried with sodium sulfate, and the solvent was removed by rotary evaporation to obtain product.

Example 5

Example Procedure (Preparation of 3-(2,3-dihydroxypropoxy)-2-hydroxypropyl 3-(3,5-di-tert-butyl-4-hydroxyphenyl)propanoate)

To a 50 mL round bottom flask with a stir bar was added 5.00 g (18.0 mmol, 1.0 eq) of 3-(3,5-di-tert-butyl-4-hydroxyphenyl)propanoic acid and 29.6 g (178 mmol, 9.9 eq) of diglycerol. A condenser and Deane-Stark trap were attached and the reaction mixture was stirred and heated under nitrogen using an oil bath at 160° C. for 10 hours. Product was extracted with ethyl acetate, organic phase was dried with sodium sulfate, and the solvent was removed by rotary evaporation to obtain product.

Example 6

Example Procedure (Preparation of 3,9-bis(((3-(3,5-di-tert-butyl-4-hydroxyphenyl)propanoyl)oxy)methyl)-3,9-dimethyl-1,5,7,11-tetraoxa-6-boraspiro[5.5]undecan-1-ium-6-uide)

To a 25 mL round bottom flask with a stir bar was added 3.00 g (7.88 mmol, 2.0 eq) of Example 4, 244 mg (3.94 mmol, 1.0 eq) of boric acid, and 6 mL of toluene. A condenser was attached and the solution was stirred under nitrogen at 95° C. for 1 hour using an oil bath. A Deane-Stark trap and light vacuum were applied before the reaction mixture was heated to 115° C. for two hours to remove water to obtain product.

Example 7

Example Procedure (Preparation of (5-methyl-2-(octyloxy)-1,3,2-dioxaborinan-5-yl)methyl 3-(3,5-di-tert-butyl-4-hydroxyphenyl)propanoate)

To a 25 mL round bottom flask with a stir bar was added 2.80 g (7.36 mmol, 1.0 eq) of Example 4, 454 mg (7.36 mmol, 1.0 eq) of boric acid, 958 mg (7.36 mmol, 1.0 eq) of 1-octanol, and 7 mL of toluene. A condenser was attached and the solution was stirred under nitrogen at 95° C. for 1 hour using an oil bath. Then, a Deane-Stark trap and light vacuum were applied and the reaction mixture was heated to 115° C. for two hours to remove water to obtain the products.

Example 8

Example Procedure (Preparation of 3-((2-((2-ethylhexyl)oxy)-1,3,2-dioxaborolan-4-yl)methoxy)-2-hydroxypropyl 3-(3,5-di-tert-butyl-4-hydroxyphenyl)propanoate)

To a 25 mL round bottom flask with a stir bar was added 3.01 g (7.04 mmol, 1.0 eq) of Example 5, 435 mg (7.04 mmol, 1.0 eq) of boric acid, 917 mg (7.04 mmol, 1.0 eq) of 2-ethylhexanol, and 7 mL of toluene. A condenser was attached and the solution was stirred under nitrogen at 95° C. for one hour using an oil bath. Then, a Deane-Stark trap and light vacuum were applied and the reaction mixture was heated to 115° C. for two hours to remove water to obtain the product.

Formulation Baseline A

A baseline lubricating oil formulation was formed containing the base formulation of Comparative Example A without the hindered phenol propionate ester antioxidant.

Comparative Example A

The natural gas engine lubricating oil composition of Comparative Example A was prepared using a base formulation containing the following additives: dispersants, detergents, wear inhibitors, foam inhibitor, and the balance, a mixture of Group I and/or II base oils. In addition to this base formulation Comparative Example A contained an antioxidant (hindered phenol propionate ester).

Example 9

A lubricating oil composition was prepared by adding the lubricating oil additive of Example 2 to the formulation baseline A.

Example 10

A lubricating oil composition was prepared by adding the lubricating oil additive of Example 3 to the formulation baseline A.

Formulation Baseline B

A baseline lubricating oil formulation was formed containing the base formulation of Comparative Example B without the hindered phenol propionate ester antioxidant.

Comparative Example B

The natural gas engine lubricating oil composition of Comparative Example B was prepared using a base formulation containing the following additives: dispersants, detergents, wear inhibitors, extreme pressure agent, foam inhibitor, the balance, a mixture of Group I and/or II base oils. In addition to this base formulation Comparative Example B contained an antioxidant (hindered phenol propionate ester).

Example 11

A lubricating oil composition was prepared by adding the lubricating oil additive of Example 2 to the formulation baseline B.

Example 12

A lubricating oil composition was prepared by adding the lubricating oil additive of Example 3 to the formulation baseline B.

The Oxidation-Nitration Test

The Oxidation-Nitration bench test demonstrates the capacity of lubricating oil to resist oxidation and nitration. This test is an additional tool to help determine the performance of oils as they relate to the actual service of lubricating engines that use natural gas as a fuel source. The lower the value for oxidation and nitration at the end of the test, the more superior the product's performance. The Oxidation-Nitration bench test was designed to simulate Caterpillar 3500 series engine conditions as related to actual field performance of the Caterpillar 3516 model. Oxidation-Nitration tests were performed on Formulation baseline A, Formulation baseline B, Example 9, Example 10, Example 11, Example 12, Comparative Example A, and Comparative Example B. The lubricating oil compositions from these Examples were placed in a heated glassware bath and subjected to calibrated levels of nitrous oxide gas over a specific period of time. The tests were run on each sample in duplicate and the results are an average of the two runs. The samples were evaluated using differential infra-red spectroscopy before placing them in the heated glassware bath to determine a base line for each sample. The samples were reevaluated at the end of testing period. The differential between the base line data, absorbance units at 5.8 and 6.1 microns, and the data taken at the end of test cycle provides an indication of the oxidation-nitration resistance of the samples.

Differential infra-red spectroscopy measures the amount of light that is absorbed by an oil sample and provides a unit of measure called an absorbance unit. DIR (Differential Infrared) spectra was determined by subtracting the fresh oil spectra from the used oil spectra to observe changes that have occurred due to oxidation, nitration, fuel dilution, soot accumulation, and or contamination. Typically a 0.1 millimeter (mm) cell is used; however an ATR crystal setup may be used after determining its associated path length. If the instrument does not have software that determines path length, the path length may be back calculated by measuring oxidation with a calibrated 0.1 mm cell. The variation between ATR and vertical cell measurements is minimal if restricted to the narrow area of oxidation and nitration (~1725 to 1630 $cm^{-1}$).

DIR Oxidation was measured from peak maximum at ~1715±5 $cm^{-1}$ to the spectra baseline (in units of absorbance).

DIR Nitration was measured from peak maximum at ~1630±1 $cm^{-1}$ to peak baseline (in units of absorbance).

Oxidation levels of 5.8 microns and Nitration levels of 6.1 microns were used as peak height comparisons.

Examples 9 and 10 perform superior to baseline A and Comparative Example A with respect to oxidation and nitration. Further, Examples 11 and 12 perform superior to baseline B and Comparative Example B with respect to oxidation, and nitration. These tests, which quantify the resistance to oxidation and nitration of lubricating oils, are used to determine whether samples are good candidates for extending the life of lubricating oils, particularly those lubricating oils for use in natural gas fueled engines. Oxidation and nitration are undesirable for lubricating oil. This concern is particularly associated with lubricating oils for use in natural gas fueled engines.

Formulation baseline A, Formulation baseline B, Example 9, Example 10, Example 11, Example 12, Comparative Example A, and Comparative Example B were tested separately by using each one as a lubricant in the bench test.

The oxidation and nitration of the samples were analyzed using differential IR as described above. Total Base Number (TBN) and Total Acid Number (TAN) analyses were also performed. TBN refers to the amount of base equivalent to milligrams of KOH in one gram of sample. Thus, higher TBN numbers reflect more alkaline products, and therefore a greater alkalinity reserve. The TBN of a sample may be determined by ASTM Test No. D2896. Higher numbers for TBN decrease indicate greater depletion of the base in the oil and are considered less favorable. TAN refers to the amount of acid equivalent to milligrams of Potassium Hydroxide (KOH) in 1 gram of sample. TAN can be determined by the procedure described in ASTM D664. Higher numbers for TAN increase indicate greater acid generation in the oil and are considered less favorable.

These results demonstrate that the lubricating oil compositions comprising the antioxidant system of this invention show high resistance to oxidation, nitration, acid development and BN depletion. The results are tabulated in Tables 2 and 3 below.

The following table shows the Oxidation-Nitration-TAN Rise-TBN Drop Performance change based on baseline formulation A.

TABLE 2

Oxidation-Nitration-Tan Rise-TBN Drop Performance Evaluation

| | Oxidation | Nitration | TAN Rise (%) | TBN Drop (%) |
|---|---|---|---|---|
| Baseline A | 127.15 | 27.855 | 11.63 | 86.03 |
| Comparative Example A | 36.47 | 20.01 | 3.635 | 81.22 |
| Example 9 | 4.6 | 2.88 | 0.79 | 50.82 |
| Example 10 | 8.42 | 13.5 | 2.13 | 49.56 |

The following table shows the Oxidation-Nitration-Tan Rise-TBN Drop Performance change based on baseline formulation B.

TABLE 3

Oxidation-Nitration-Tan Rise-TBN Drop Performance Evaluation

| | Oxidation | Nitration | TAN Rise (%) | TBN Drop (%) |
|---|---|---|---|---|
| Baseline B | 94.34 | 23.67 | 10.33 | 86.11 |
| Comparative Example B | 10.645 | 3.585 | 2.25 | 66.23 |
| Example 11 | 5.79 | 2.29 | 0.22 | 42.97 |
| Example 12 | 5.96 | 1.89 | 0.56 | 50.48 |

Friction Performance

High Frequency Reciprocating Rig (HFRR) Evaluation

The compositions described above were tested for friction performance in a HFRR bench test from 40° C. to 180° C.

The friction performance of the lubricating oil composition of Example 9 containing the lubricating oil additive of Example 2 and the lubricating oil composition of Example 10 containing the lubricating oil additive of Example 3 was evaluated using a High Frequency Reciprocating Rig (HFRR), and compared to the friction performance of the lubricating oil composition of Comparative Example A.

The HFRR test rig is an industry recognized tribometer for determining lubricant performance. The PCS instrument uses an electromagnetic vibrator to oscillate a specimen (the ball) over a small amplitude while pressing it against a fixed specimen (a flat disk). The amplitude and frequency of the oscillation and the load are variable. The frictional force between the ball and flat and the electrical contact resistance (ECR) are measured. The flat, stationary specimen is held in a bath to which the lubricating oil is added, and can be heated. For this test, the tribometer was set up to run at 20 Hz for 20 minutes, using 6 mm ball on flat specimens of 52100 steel. The load was 1 kg and temperature was conducted at 40° C., 60° C., 80° C., 100° C., 120° C., 140° C., 160° C., and 180° C. The lubricating oils were pretreated with about 6% by weight, based on the total weight of lubricating oil, of diesel engine soot collected from diesel engine exhaust. The soot was stirred into the oil to wet it and then homogenized for 15 minutes prior to testing. In this test, a smaller coefficient of friction corresponds to a more effective lubricating friction modifier additive. The HFRR friction performance data are represented in Table 4. The table shows the HFRR 40-180 performance evaluation based on baseline formulation A. The average coefficients of friction are tabulated below.

TABLE 4

HFRR 40-180 performance evaluation

| Oil Temperature | 40° C. | 60° C. | 80° C. | 100° C. | 120° C. | 140° C. | 160° C. | 180° C. |
|---|---|---|---|---|---|---|---|---|
| Comparative Example A | 0.1365 | 0.1535 | 0.173 | 0.1935 | 0.2075 | 0.2135 | 0.2105 | 0.2005 |
| Example 9 | 0.1345 | 0.151 | 0.161 | 0.167 | 0.171 | 0.1745 | 0.179 | 0.1825 |
| Example 10 | 0.1245 | 0.132 | 0.151 | 0.1645 | 0.167 | 0.1675 | 0.1615 | 0.1655 |

As the data in Table 4 show, the Examples 9 and 10 of the present invention demonstrates significantly better anti-friction properties than Comparative Example A at temperatures from 100 to 180° C.

The friction performance of the lubricating oil composition of Example 11 containing the lubricating oil additive of Example 2 and the lubricating oil composition of Example 12 containing the lubricating oil additive of Example 3 was evaluated using a High Frequency Reciprocating Rig (HFRR), and compared to the friction performance of the lubricating oil composition of Comparative Example B. The HFRR friction performance data are represented in Table 5. The table shows the HFRR 40-180 performance evaluation based on baseline formulation B. The average coefficients of friction are tabulated below.

TABLE 5

HFRR 40-180 performance evaluation

| Oil Temperature | 40° C. | 60° C. | 80° C. | 100° C. | 120° C. | 140° C. | 160° C. | 180° C. |
|---|---|---|---|---|---|---|---|---|
| Comparative Example B | 0.134 | 0.148 | 0.1675 | 0.175 | 0.184 | 0.1935 | 0.1965 | 0.1935 |
| Example 11 | 0.1325 | 0.141 | 0.156 | 0.142 | 0.167 | 0.1745 | 0.175 | 0.181 |
| Example 12 | 0.1165 | 0.1175 | 0.13 | 0.1485 | 0.1685 | 0.1735 | 0.1705 | 0.167 |

As the data in Table 5 show, Examples 11 and 12 of the present invention demonstrate significantly better anti-friction properties than Comparative Example B at temperatures from 100 to 180° C.

MTM Bench Test

The compositions described above were tested for friction performance in a Mini-Traction Machine (MTM) bench test. The MTM is manufactured by PCS Instruments and operates with a ball (0.75 inches 8620 steel ball) loaded against a rotating disk (52100 steel). The conditions employ a load of approximately 10-30 Newtons, a speed of approximately 10-2000 mm/s and a temperature of approximately 125-150° C. In this bench test, friction performance is measured as the comparison of the total area under the second Stribeck curve generated with the baseline formulation and the second Stribeck curve generated with the baseline formulation top-treated with a friction modifier. Lower total area values correspond to better friction performance of the oil. Average Coefficient of Friction was measured vs. Log (mean speed), mm/s for the lubricating oil composition of Example 9 and the lubricating oil composition of Example 10 and compared to that of the lubricating oil composition of Comparative Example A.

TABLE 6

Frictional Properties

| Formulation | ΔArea (avg.) b/w two Stribeck curves |
|---|---|
| Comparative Example A | 1.222 |
| Example 9 | −2.641 |
| Example 10 | −1.623 |

As the data in Table 6 show, Examples 9 and 10 of the present invention demonstrate significantly better anti-friction properties than Comparative Example A. This should indicate fuel economy and fuel economy retention.

The MTM bench test was conducted as described above. Average Coefficient of Friction was measured vs. Log (mean speed), mm/s for the lubricating oil composition of Example 11 and the lubricating oil composition of Example 12 and compared to that of the lubricating oil composition of Comparative Example B.

TABLE 7

Frictional Properties

| Formulation | ΔArea (avg.) b/w two Stribeck curves |
|---|---|
| Comparative Example B | −0.454 |
| Example 11 | 2.190 |
| Example 12 | −1.392 |

As the data in Table 7 shows, Example 12 of the present invention demonstrates significantly better anti-friction properties than Comparative Example B. This should indicate fuel economy and fuel economy retention.

Friction Retention Post Oxidation/Nitration

The MTM bench test was conducted as described above. Average Coefficient of Friction was measured vs. Log (mean speed), mm/s for the lubricating oil composition of Example 9 and the lubricating oil composition of Example 10 and compared to that of the lubricating oil composition of Comparative Example A to measure friction retention post oxidation/nitration performance evaluation as area under the Stribeck curves for fresh oil and post oxidation/nitration oil.

TABLE 8

Frictional Properties

| Formulation | Avg. area under $1^{st}$ Stribeck curve of fresh oil | Avg. area under $1^{st}$ Stribeck curve of post oxidation/nitration oil | ΔArea (avg.) b/w two Stribeck curves |
|---|---|---|---|
| Comparative Example A | 58.90 | 53.96 | −4.95 |
| Example 9 | 58.74 | 52.06 | −6.68 |
| Example 10 | 55.44 | 53.71 | −1.73 |

As the data in Table 8 show, Example 9 of the present invention demonstrates significantly better anti-friction properties after oxidation/nitration than Comparative Example A.

Average Coefficient of Friction was measured vs. Log (mean speed), mm/s for the lubricating oil composition of Example 11 and the lubricating oil composition of Example 12 and compared to that of the lubricating oil composition of Comparative Example B to measure friction retention post oxidation/nitration performance evaluation as area under the Stribeck curves for fresh oil and post oxidation/nitration oil.

TABLE 9

| Formulation | Avg. area under 1st Stribeck curve of fresh oil | Avg. area under 1st Stribeck curve of post oxidation/ nitration oil | ΔArea (avg.) b/w two Stribeck curves |
|---|---|---|---|
| Comparative Example B | 58.84 | 57.10 | −1.74 |
| Example 11 | 58.58 | 53.49 | −5.09 |
| Example 12 | 56.01 | 56.21 | 0.20 |

As the data in Table 9 shows, Example 11 of the present invention demonstrates significantly better anti-friction properties after oxidation/nitration than Comparative Example B.

Example 13

A lubricating oil composition was prepared by adding the lubricating oil additive of Example 8 (1% treat rate) to the formulation baseline A.

Mixed Regime Friction Testing

The MTM bench test was conducted as described in previously. Average Coefficient of Friction was measured vs. Log (mean speed), mm/s for the lubricating oil composition of Example 13 and compared to that of the lubricating oil composition of Comparative Example A.

TABLE 10

| Formulation | ΔArea (avg.) b/w two Stribeck curves |
|---|---|
| Comparative Example A | −4.95 |
| Example 13 | −16 |

As the data in Table 10 show, Example 20 of the present invention demonstrate significantly better anti-friction properties, fuel economy, and fuel economy retention than Comparative Example A.

Formulation Baseline C

The railroad engine lubricating oil composition of Comparative Example C was prepared using the following additives: dispersants, detergents, wear inhibitors, corrosion inhibitor, foam inhibitor, VII, and the balance, base oils.

Comparative Example C

A lubricating oil composition was prepared by adding a hindered phenolic ester antioxidant to Formulation Baseline C.

Example 14

A lubricating oil composition was prepared by adding the lubricating oil additive of Example 2 to Formulation Baseline C.

Formulation Baseline C, Comparative Example C, and Example 14 of the invention were tested in the B2-7 which is otherwise known as the Union Pacific (UP) Oxidation Test. This test method is described below.

B2-7 Test/Union Pacific Oxidation Test

The B2-7 test is an oxidation test with the following conditions:

UP Oxidation Test (B2)

| | |
|---|---|
| Temp | 149 C. (300 F.) |
| Duration | 96 hr |
| Coupons | Cu, Fe, Pb |
| Flow | Oxygen |
| Replenishing oil | At 48 hr (50 mL), 72 hr (50 mL) |
| Comments | Trend data of BN, AN, pH, Pb and Cu ppm |

According to the B2-7 test, the oil to be tested is heated at 300° F. for 96 hours with bubbling oxygen. Copper, iron and lead coupons are suspended in the oil. Fifty milliliter samples are taken at 48, 72 and 96 hours. The samples at 48 and 72 hours are replenished with fresh oil. The oil test samples are evaluated for base number, acid number, pH, lead, and copper.

Table 11 shows the B2-7 Performance change for Formulation Baseline C, Comparative Example C, and Example 14.

TABLE 11

| | B2-7 Performance Evaluation | | | | |
|---|---|---|---|---|---|
| | TBN Decrease (mg/KOH) | TAN Increase | pH Change | Pb (ppm) | Cu (ppm) |
| Formulation Baseline C | 5.28 | 2.17 | 3.53 | 3073 | 7 |
| Comparative Example C | 5.04 | 2.14 | 3.19 | 3180 | 7 |
| Example 14 | 4.98 | 1.73 | 3.16 | 1592 | 7 |

The samples in the comparative examples (Formulation Baseline C and Comparative Example C) and samples in the examples of the invention (Examples 14) were evaluated for Total Base Number (TBN) decrease, TAN increase, pH change, lead corrosion, and copper corrosion which is measured as parts per million of lead and copper found in the oil (i.e., Pb and Cu ppm), respectively. Higher numbers for TBN decrease indicate greater depletion of the base in the oil and are considered less favorable. Similarly, higher numbers for Pb (ppm) indicate greater lead corrosion and are considered less favorable. An oil for extended use in a locomotive diesel engine will ideally retain TBN and not show corrosion against lead.

B2-7 Results

Based upon the results of the test it is evident that the lubricating oil compositions of Example 14 exhibits a lower number for TBN decrease, thus indicating that the base in the lubricating oil is not depleted as much as in Formulation Baseline C and Comparative Example C. Example 14 also exhibits less acid generation than as in Formulation Baseline C and Comparative Example C.

Additionally, lead corrosion has decreased in the samples of the oils of Example 14. The amount of lead corrosion is low, especially when compared to the lead corrosion results of the oils that are Formulation Baseline C and Comparative Example C.

Example 15

Example Procedure (Preparation of 7-(((3-(3,5-di-tert-butyl-4-hydroxyphenyl)propanoyl)oxy)methyl)-3-(hydroxymethyl)-1,4,6,9-tetraoxa-5-boraspiro[4.4]nonan-1-ium-5-uide)

To a 10 mL round bottom flask was added and 0.9322 g (10.0 mmol, 2.0 eq) of glycerol and 0.313 g (5.0 mmol, 1.0 eq) of boric acid. The reaction mixture was stirred under a weak nitrogen stream while being heated at 90° C. for 15 min. The water was removed by distillation and the mixture was heated to 190° C. and 1.4 g (5.029 mmol, 1.0 eq) of 3-(3,5-di-tert-butyl-4-hydroxyphenyl)propionic acid was added and allowed to stir for 7 h at 190° C. and cooled to room temperature to obtain product.

Example 16

Example Procedure (Preparation of 3,7-bis(((3-(3,5-di-tert-butyl-4-hydroxyphenyl)propanoyl)oxy)methyl)-1,4,6,9-tetraoxa-5-boraspiro[4,4]nonan-1-ium-5-uide): Alternate Procedure To a reactor fitted with a Deane-Stark trap can be added approximately 2 equivalents of polyol (i.e., glycerol) to 1 equivalent of boron containing compound (e.g., boric acid) in a solvent (e.g., toluene). The reaction mixture can be stirred under a weak nitrogen stream while heated at a temperature and time sufficient to form a borated complex. To this can be added approximately 2 equivalents (for every equivalent of boron) of a phenolic acid or ester (e.g., 3-(3,5-di-tert-butyl-4-hydroxyphenyl)propanoic acid) at a temperature and time sufficient to form a compound similar to that described in Example 3. The reaction will proceed via dehydration if phenolic acid is selected and under esterification if phenolic ester is selected.

Example 17

Example Procedure (Preparation of 7-(((3-(3,5-di-tert-butyl-4-hydroxyphenyl)propanoyl)oxy)methyl)-3-(hydroxymethyl)-1,4,6,9-tetraoxa-5-boraspiro[4.4]nonan-1-ium-5-uide): Alternate procedure To a reactor fitted with a Deane-Stark trap can be added approximately 2 equivalents of polyol (i.e., glycerol) and approximately 1 equivalent of boron containing compound (e.g., boric acid) in a solvent (e.g., toluene). The reaction mixture can be stirred under a weak nitrogen stream while heated at a temperature and time sufficient to form a borated complex. To this can be added approximately 1 equivalent a phenolic acid or ester (e.g., 3-(3,5-di-tert-butyl-4-hydroxyphenyl)propanoic acid) at a temperature and time sufficient to form a compound similar to that described in Example 15. The reaction will proceed via dehydration if phenolic acid is selected and under esterification if phenolic ester is selected.

The lubricating oil compositions comprising a compound of the present invention demonstrate a significant improvement with regard to both BN retention and lead corrosion over oils which do not contain a compound of the present invention.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. A compound comprising the reaction product of:
   a. a phenolic ester polyol, wherein the phenolic ester polyol has the following formula (I):

Formula (I)

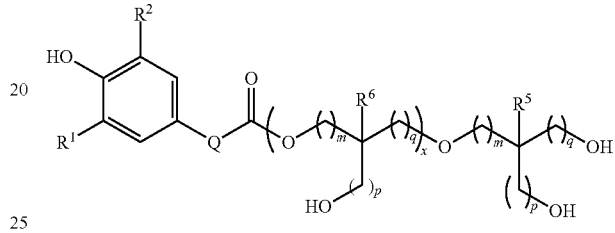

wherein Q is an alkylene group of 2 to 6 carbon atoms; each m is independently 1, 2, or 3; each p is independently 0, 1, 2, or 3; each q is independently 0, 1, 2, or 3; x is 0, 1, or 2; $R^1$ and $R^2$ are each independently a $C_1$-$C_{12}$ alkyl group; $R^5$ is H, a $C_1$-$C_{12}$ alkyl group, or a $C_1$-$C_3$ alkanol; and $R^6$ is H, a $C_1$-$C_{12}$ alkyl group, or a $C_1$-$C_3$ alkanol;
   b. a boron containing compound; and
   c. optionally, an alcohol.

2. The compound of claim 1, wherein the phenolic ester polyol is selected from the group consisting of a glycerol ester of a propionate phenol, diglycerol ester of a propionate phenol, pentaerythritol ester of a propionate phenol, and a trimethylolethane ester of a propionate phenol.

3. The compound of claim 1, wherein the alcohol is a linear or branched aliphatic alcohol.

4. The compound of claim 1, wherein the alcohol is a monool or polyol.

5. A compound having the following formula (IV):

Formula (IV)

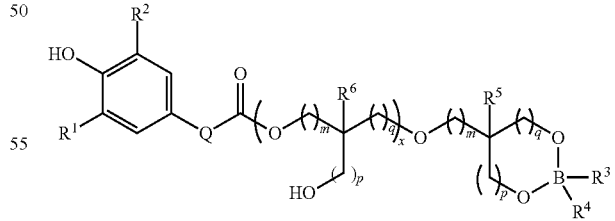

wherein Q is an alkylene group of 2 to 6 carbon atoms; each m is independently 1, 2, or 3; each p is independently 0, 1, 2, or 3; each q is independently 0, 1, 2, or 3; x is 0, 1, or 2; $R^1$ and $R^2$ are each independently a $C_1$-$C_{12}$ alkyl group; $R^3$ is absent or a $C_1$-$C_{12}$ alkoxy group; $R^4$ is absent or a $C_1$-$C_{12}$ alkoxy group; $R^5$ is H, a $C_1$-$C_{12}$ alkyl group, or a $C_1$-$C_3$ alkanol; and $R^6$ is H, a $C_1$-$C_{12}$ alkyl group, or a $C_1$-$C_3$ alkanol.

6. A compound having the following formula (V):

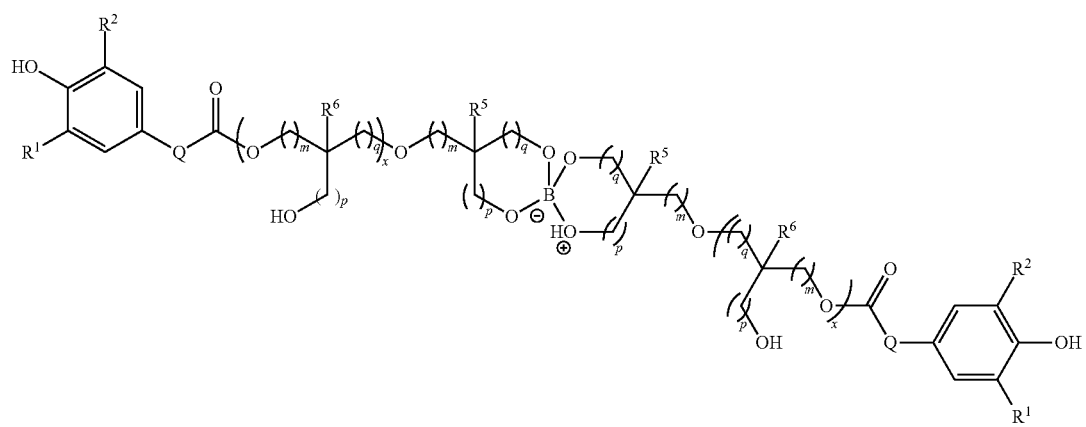

Formula (V)

wherein Q is an alkylene group of 2 to 6 carbon atoms; each m is independently 1, 2, or 3; each p is independently 0, 1, 2, or 3; each q is independently 0, 1, 2, or 3; x is 0, 1, or 2; $R^1$ and $R^2$ are each independently a $C_1$-$C_{12}$ alkyl group; $R^5$ is H, a $C_1$-$C_{12}$ alkyl group, or a $C_1$-$C_3$ alkanol; and $R^6$ is H, a $C_1$-$C_{12}$ alkyl group, or a $C_1$-$C_3$ alkanol.

7. The compound of claim 5, wherein the compound has the following formula (VI):

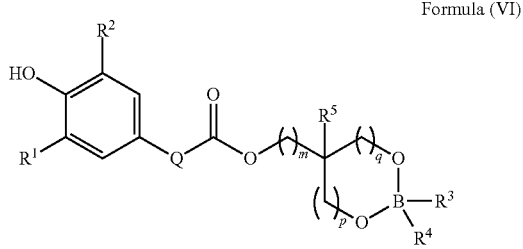

Formula (VI)

wherein $R^1$, $R^2$, $R^3$, $R^4$, $R^5$, m, p, and q are as defined in claim 5.

8. The compound of claim 5, wherein the compound has the following formula (VII):

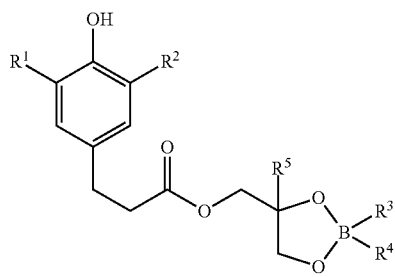

Formula (VII)

wherein $R^1$, $R^2$, $R^3$, $R^4$, and $R^5$ are as defined in claim 5.

9. The compound of claim 5, wherein the compound has the following structure (VIII):

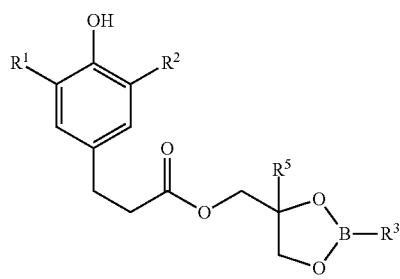

Formula (VIII)

wherein $R^1$, $R^2$, $R^3$, and $R^5$ are as defined in claim 5.

10. The compound of claim 6, wherein the compound has the structure of formula (IX):

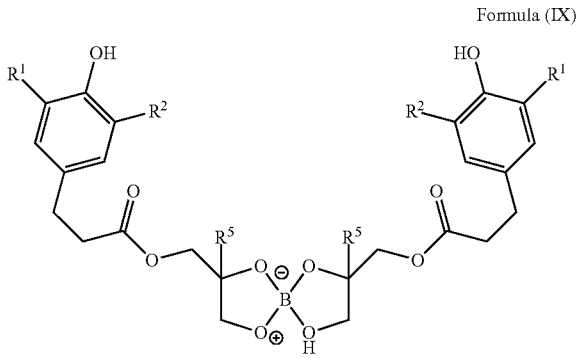

Formula (IX)

wherein $R^1$, $R^2$, and $R^5$ are as defined in claim 6.

11. The compound of claim 5, wherein $R^1$ and $R^2$ are both t-butyl groups.

12. The compound of claim 6, wherein $R^1$ and $R^2$ are both t-butyl groups.

13. A compound comprising the reaction product of:
a. a polyol,
b. a boron containing compound, and
c. a phenolic acid or ester, wherein the polyol has the following formula (III):

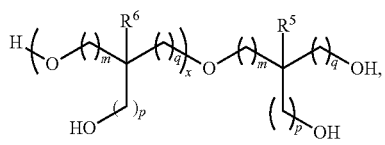

(Formula III)

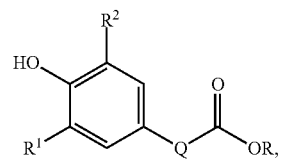

(Formula II)

wherein Q is an alkylene group of 2 to 6 carbon atoms; R is H or a moiety suitable to undergo transesterification; $R^1$ and $R^2$ are each independently a $C_1$-$C_{12}$ alkyl group.

14. The compound of claim 13, wherein the molar ratio of boron containing compound:polyol:phenolic acid or ester is about 1:2:2.

15. The compound of claim 13, wherein the molar ratio of boron containing compound:polyol:phenolic acid or ester is about 1:2:1.

wherein each m is independently 1, 2, or 3; each p is independently 0, 1, 2, or 3; each q is independently 0, 1, 2, or 3; x is 0, 1, or 2; $R^5$ is H, a $C_1$-$C_{12}$ alkyl group, or a $C_1$-$C_3$ alkanol; and $R^6$ is H, a $C_1$-$C_{12}$ alkyl group, or a $C_1$-$C_3$ alkanol; and the phenolic acid or ester has the following formula (II):

* * * * *